(12) United States Patent
DiPoto et al.

(10) Patent No.: US 7,144,393 B2
(45) Date of Patent: *Dec. 5, 2006

(54) STRUCTURE FOR RECEIVING SURGICAL INSTRUMENTS

(76) Inventors: Gene P. DiPoto, 23 Crocket Rd., Upton, MA (US) 01568; William Silver, 9 Draper Rd., Millbury, MA (US) 01527; John D. Unger, 20 Farm Hill Rd., Wrentham, MA (US) 02093

( * ) Notice: Subject to any disclaimer, the term of this patent is extended or adjusted under 35 U.S.C. 154(b) by 0 days.

This patent is subject to a terminal disclaimer.

(21) Appl. No.: 10/361,887

(22) Filed: Feb. 10, 2003

(65) Prior Publication Data

US 2003/0153927 A1   Aug. 14, 2003

Related U.S. Application Data

(63) Continuation-in-part of application No. 09/855,358, filed on May 15, 2001, now Pat. No. 6,524,320.

(51) Int. Cl.
*A61B 17/00* (2006.01)
*A61B 29/00* (2006.01)

(52) U.S. Cl. ............... 606/1; 606/198; 606/191
(58) Field of Classification Search .......... 606/1, 606/191, 198, 184, 185; 604/104, 105
See application file for complete search history.

(56) References Cited

U.S. PATENT DOCUMENTS

| | | |
|---|---|---|
| 151,228 A | 5/1874 | Knafil |
| 530,728 A | 12/1894 | Sherbrook |
| 1,170,324 A | 2/1916 | Pomerene |
| 2,083,573 A | 6/1937 | Morgan |
| 2,313,164 A | 3/1943 | Nelson |
| 2,594,086 A | 4/1952 | Smith |

(Continued)

FOREIGN PATENT DOCUMENTS

DE   202 16 712 U 1   3/2003

(Continued)

OTHER PUBLICATIONS

A manual entitled MED™—MicroEndoscopic Discectomy System by Sofamor Danek USA, dated 1996 (pp. 1-33).

(Continued)

*Primary Examiner*—Vy Q. Bui
(74) *Attorney, Agent, or Firm*—Knobbe Martens Olson & Bear LLP

(57) ABSTRACT

A structure for receiving surgical instruments for performing a surgical procedure on a body includes a passage through which the surgical instruments are inserted into the body. The passage has a proximal end and a distal end. An expandable portion enables an increase in the cross-sectional area of the distal end of the passage. The expandable portion has a contracted condition in which the cross-sectional area of the distal end of the passage has a first cross-sectional area. The expandable portion has an expanded condition in which the distal end of the passage has a second cross-sectional area greater than the first cross-sectional area. The second cross-sectional area is greater than a cross-sectional area of the proximal end of the passage when the expandable portion is in the expanded condition. A retaining mechanism resists movement of the expandable portion from the expanded condition toward the contracted condition during the surgical procedure. The retaining mechanism is released at the conclusion of the surgical procedure to permit movement of the expandable portion from the expanded condition toward the contracted condition for removal of the structure.

91 Claims, 12 Drawing Sheets

U.S. PATENT DOCUMENTS

| | | | |
|---|---|---|---|
| 2,623,517 A | 12/1952 | Barlow et al. |
| 3,044,461 A | 7/1962 | Murdock |
| 3,070,088 A | 12/1962 | Brahos |
| 3,503,398 A | 3/1970 | Fogarty et al. |
| 3,509,873 A | 5/1970 | Karlin et al. |
| 3,749,088 A | 7/1973 | Kohlmann |
| 3,789,852 A | 2/1974 | Kim et al. |
| 3,965,890 A | 6/1976 | Gauthier |
| 3,998,217 A | 12/1976 | Trumbull et al. |
| 4,010,741 A | 3/1977 | Gauthier |
| 4,130,113 A | 12/1978 | Graham |
| 4,155,355 A | 5/1979 | Yamamoto |
| 4,254,763 A | 3/1981 | McCready et al. |
| 4,421,107 A | 12/1983 | Estes et al. |
| 4,449,532 A | 5/1984 | Storz |
| 4,451,256 A | 5/1984 | Weikl et al. |
| 4,545,374 A | 10/1985 | Jacobson |
| 4,573,448 A | 3/1986 | Kambin |
| 4,601,713 A | 7/1986 | Fuqua |
| 4,716,901 A | 1/1988 | Jackson et al. |
| 4,863,133 A | 9/1989 | Bonnell |
| 4,899,729 A | 2/1990 | Gill et al. |
| 4,921,478 A | 5/1990 | Solano et al. |
| 4,984,564 A | 1/1991 | Yuen |
| 5,139,511 A | 8/1992 | Gill et al. |
| 5,163,949 A | 11/1992 | Bonutti |
| 5,183,464 A | 2/1993 | Dubrul et al. |
| 5,190,561 A | 3/1993 | Graber |
| 5,196,023 A | 3/1993 | Martin |
| 5,197,971 A | 3/1993 | Bonutti |
| 5,231,974 A | 8/1993 | Giglio et al. |
| 5,295,994 A | 3/1994 | Bonutti |
| 5,312,417 A | 5/1994 | Wilk |
| 5,313,962 A | 5/1994 | Obenchain |
| 5,318,588 A | 6/1994 | Horzewski et al. |
| 5,345,927 A | 9/1994 | Bonutti |
| 5,354,302 A | 10/1994 | Ko |
| 5,370,647 A | 12/1994 | Graber et al. |
| 5,370,659 A | 12/1994 | Sakashita |
| 5,395,317 A | 3/1995 | Kambin |
| 5,400,774 A | 3/1995 | Villalta et al. |
| 5,417,203 A | 5/1995 | Tovey et al. |
| 5,439,464 A | 8/1995 | Shapiro |
| 5,443,479 A | 8/1995 | Bressi, Jr. |
| 5,454,365 A | 10/1995 | Bonutti |
| 5,490,819 A | 2/1996 | Nicholas et al. |
| 5,503,617 A | 4/1996 | Jako |
| 5,505,690 A | 4/1996 | Patton et al. |
| 5,529,571 A | 6/1996 | Daniel |
| 5,573,517 A | 11/1996 | Bonutti et al. |
| 5,601,590 A | 2/1997 | Bonutti et al. |
| 5,667,481 A | 9/1997 | Villalta et al. |
| 5,667,520 A | 9/1997 | Bonutti |
| 5,681,265 A | 10/1997 | Maeda et al. |
| 5,688,223 A | 11/1997 | Rosendahl |
| 5,690,606 A | 11/1997 | Slotman |
| 5,707,359 A | 1/1998 | Bufalini |
| 5,728,046 A | 3/1998 | Mayer et al. |
| 5,762,629 A | 6/1998 | Kambin |
| 5,782,919 A | 7/1998 | Zdeblick et al. |
| 5,792,044 A | 8/1998 | Foley et al. |
| 5,795,289 A | 8/1998 | Wyttenbach |
| 5,795,291 A | 8/1998 | Koros et al. |
| 5,813,978 A | 9/1998 | Jako |
| 5,827,319 A | 10/1998 | Carlson et al. |
| 5,851,214 A | 12/1998 | Larsen et al. |
| 5,865,802 A | 2/1999 | Yoon et al. |
| 5,868,668 A | 2/1999 | Weiss |
| 5,902,231 A | 5/1999 | Foley et al. |
| 5,944,658 A | 8/1999 | Koros et al. |
| 5,954,635 A | 9/1999 | Foley et al. |
| 5,961,499 A | 10/1999 | Bonutti et al. |
| 5,976,146 A | 11/1999 | Ogawa et al. |
| 5,976,161 A | 11/1999 | Kirsch et al. |
| 5,997,508 A | 12/1999 | Lunn et al. |
| 6,024,697 A | 2/2000 | Pisarik |
| 6,083,154 A | 7/2000 | Liu et al. |
| 6,096,046 A | 8/2000 | Weiss |
| 6,120,437 A | 9/2000 | Yoon et al. |
| 6,126,671 A | 10/2000 | Richards et al. |
| 6,139,493 A | 10/2000 | Koros et al. |
| 6,152,871 A | 11/2000 | Foley et al. |
| 6,162,236 A | 12/2000 | Osada |
| 6,171,299 B1 | 1/2001 | Bonutti |
| 6,175,758 B1 | 1/2001 | Kambin |
| 6,187,000 B1 | 2/2001 | Davison et al. |
| 6,206,826 B1 | 3/2001 | Mathews et al. |
| 6,224,545 B1 | 5/2001 | Cocchia et al. |
| 6,312,443 B1 | 11/2001 | Stone |
| 6,338,730 B1 | 1/2002 | Bonutti et al. |
| 6,354,995 B1 | 3/2002 | Hoftman et al. |
| 6,358,266 B1 | 3/2002 | Bonutti |
| 6,361,488 B1 | 3/2002 | Davidson et al. |
| 6,371,968 B1 | 4/2002 | Kagasaka et al. |
| 6,383,195 B1 | 5/2002 | Richard |
| 6,464,634 B1 | 10/2002 | Fraser |
| 6,494,893 B1 | 12/2002 | Dubrul et al. |
| 6,524,320 B1 | 2/2003 | DiPoto |
| 6,530,880 B1 | 3/2003 | Pagliuca |
| 6,530,926 B1 | 3/2003 | Davison |
| 6,616,605 B1 | 9/2003 | Wright et al. |
| 6,648,888 B1 | 11/2003 | Shluzas |
| 6,652,553 B1 | 11/2003 | Davison et al. |
| 6,712,795 B1 | 3/2004 | Cohen |
| 6,800,084 B1 | 10/2004 | Davison et al. |
| 2001/0049498 A1 | 12/2001 | Davison et al. |
| 2002/0002360 A1 | 1/2002 | Stecker et al. |
| 2003/0009130 A1 | 1/2003 | Bonutti et al. |
| 2003/0014068 A1 | 1/2003 | Bonutti et al. |
| 2003/0040656 A1 | 2/2003 | Pagliuca et al. |
| 2003/0073998 A1 | 4/2003 | Pagliuca et al. |
| 2003/0097045 A1 | 5/2003 | Kashyap |
| 2003/0153911 A1 | 8/2003 | Shluzas |
| 2003/0153927 A1 | 8/2003 | DiPoto et al. |
| 2003/0167058 A1 | 9/2003 | Shluzas |
| 2003/0191371 A1 | 10/2003 | Smith et al. |
| 2003/0236529 A1 | 12/2003 | Shluzas et al. |
| 2004/0002629 A1 | 1/2004 | Branch et al. |
| 2004/0093001 A1 | 5/2004 | Hamada |
| 2004/0176665 A1 | 9/2004 | Branch et al. |

FOREIGN PATENT DOCUMENTS

| | | |
|---|---|---|
| EP | 0807415 A2 | 5/1997 |
| WO | WO 95/22285 | 8/1995 |
| WO | WO 01/54560 A2 | 2/2001 |

OTHER PUBLICATIONS

Atlantis Surgical, Jakoscope® Minimally Invasive Direct Access Surgical Technology, leaflet.

Jako, G.J. et al., Development of minimally invasive direct access surgical technology, The British Journal of Surgery, vol. 85, Supplement, Jul. 2, 1998, pp. 208-210—Eurosurgery 98, Budapest, Hungary, Jun. 17-20 1998, Blackwell Science.

Warnock, Scott, Jakoscope allows better view, smaller incisions for ALIF, Orthopedics Today.

Jako, Geza J. et al., Minimally Invasive Direct Access Surgical Technology—MIDAST, Surgical Technology International VIII, pp. 111-119.

Howard, Douglas R. et al., Minimal and Direct Access to the Anterior Lumbar Spine, Howard-Jako Technique for MIDAS-ALIF, 1996-1997, Atlantis Surgical.

Caspar, Wolfhard, M.D. et al., The Caspar Microsurgical Discectomy and Comparison with a Conventional Standard Lumber Disc Procedure, Neurosurgery, vol. 28, Nov. 1, 1991.

Bookwalter Retractor Kit II, by Codman, Johnson & Johnson, 1997.

Balfour Retractors and Blades Catalog, 1997.

Foley, Kevin T., M.D., et al. Neurosurg Focus, 10:1-8, 2001 "Pecutaneous Pedicle Screw Fixation of the Lumber Spine".

Guiot, Bernard H., M.D. et al., Spine, 27, 4:432-438, 2002 "A Minimally Invasive Technique of Decompression of the Lumbar Spine".

Kambin, Parviz, Publisher Unknown, Chapter 77:1055-1066, Date Unknown "Arthroscopic Lumbar Interbody Fusion".

Kambin, Parviz, Publisher Unknown, Chapter 9:117-121, Date Unknown "Posterolateral Percutaneous Lumbar Interbody Fusion".

Medtronic Sofamor Danek, METRx MicroEndoscopic Discectomy, 1999 "An Evolution in Minimally Invasive Spine Surgery".

Medtronic Sofamor Danek, METRx MicroDiscectomy System, 2002 "The Next Step in Minimially Invasive Discectomy Utilizing the Operating Microscope".

Medtronic Sofamor Danek, METRx Microdiscectomy Surgical Technique, 2001 as described by Donald L. Hilton, Jr., M.D., F.A.C.S. and Sylvain Palmer, M.D., F.A.C.S.

Medtronic Sofamor Danek, Orthopedics Today, 1-20, 2002 "Minimal Access Spinal Technologies".

Stauber, Martin H. M.D. et al., Spine, 19, 1:57-61; 1994 "Pedicle Screw Placement with Intraosseous Endocopy".

Ditsworth, David A., M.D., Surg Nerol, 49; 588-598, 1998 Endoscopic Transforaminal Lumbar Discectomy and Reconfiguration: A Postero-lateral Approach into the Spinal Canal.

Endius Marketing Bulletin, 2002, Atavi Atraumatic Spine Fusion System, "How Do I Decompress Using Atavi System?".

Endius Marketing Bulletin, 2002, Atavi Atraumatic Spine Fusion System, "Minimally Invasive Update on Danek".

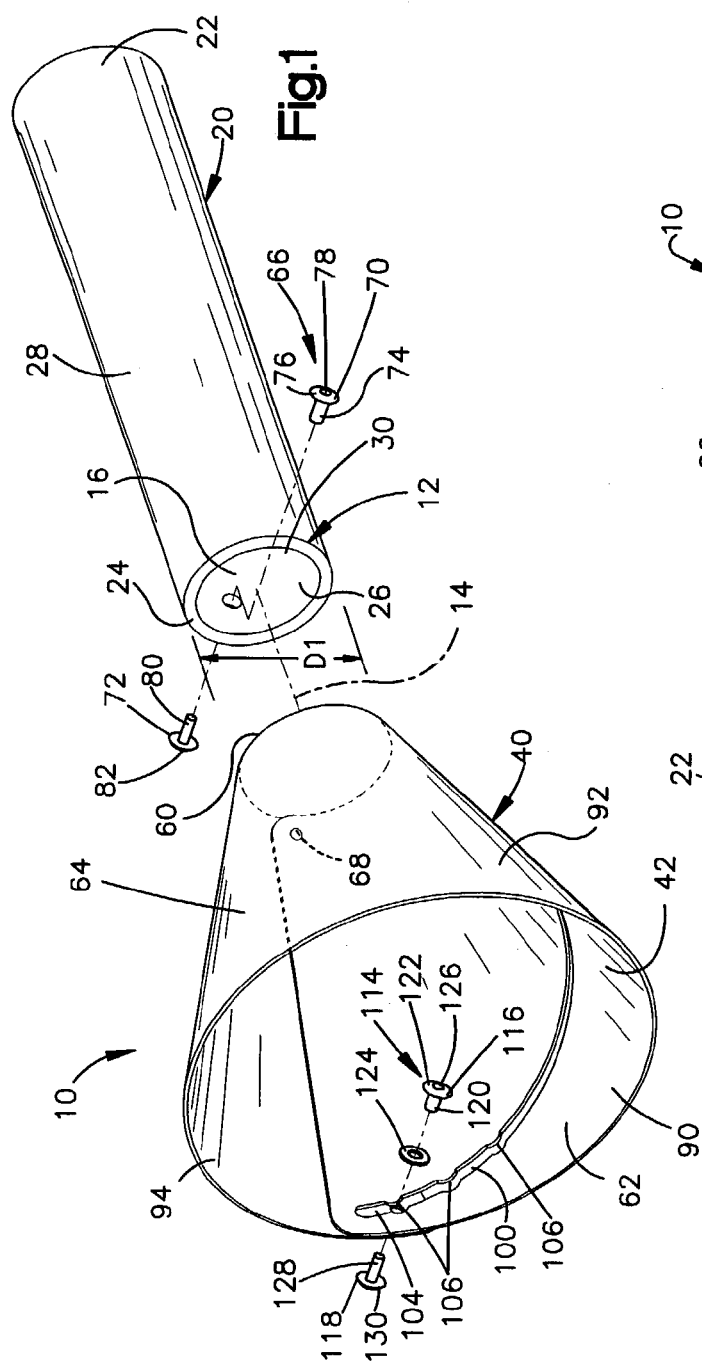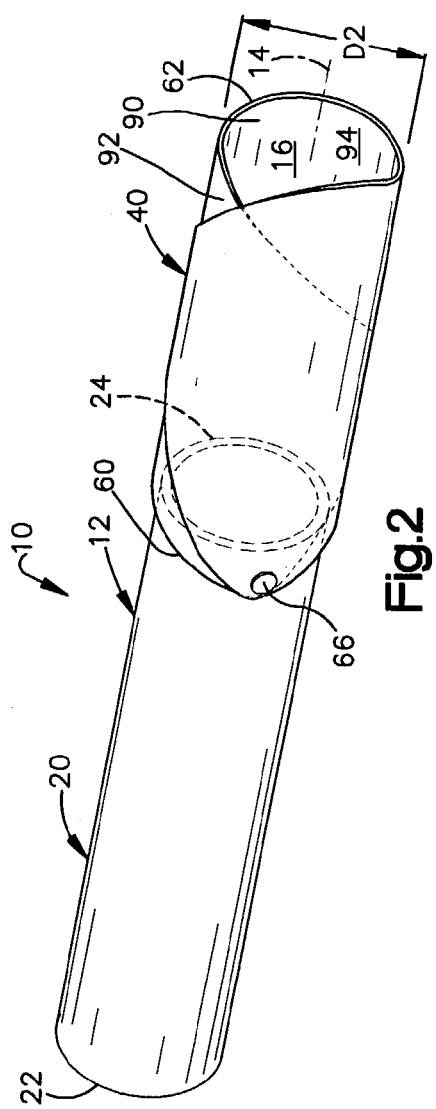

US 7,144,393 B2

STRUCTURE FOR RECEIVING SURGICAL INSTRUMENTS

CROSS-REFERENCE TO RELATED APPLICATION

This application is a continuation-in-part of U.S. patent application Ser. No. 09/855,358, filed on May 15, 2001 now U.S. Pat. No. 6,524,320.

FIELD OF THE INVENTION

The present invention relates to a structure for receiving surgical instruments for performing a surgical procedure on a body.

BACKGROUND OF THE INVENTION

A known structure for receiving surgical instruments is disclosed in U.S. Pat. No. 6,187,000. U.S. Pat. No. 6,187,000 discloses a cannula having an expandable portion. The expandable portion has a slot and a guide member disposed in the slot. The guide member is movable from a first terminal end of the slot to a second terminal end of the slot to enable the cross-sectional area of a passage in the cannula to increase.

SUMMARY OF THE INVENTION

The present invention is a structure for receiving surgical instruments for performing a surgical procedure on a body. The structure includes a passage through which the surgical instruments are inserted into the body. The passage has a proximal end and a distal end. An expandable portion enables an increase in a cross-sectional area of the distal end of the passage.

The expandable portion has a contracted condition in which the cross-sectional area of the distal end of the passage has a first cross-sectional area. The expandable portion has an expanded condition in which the distal end of the passage has a second cross-sectional area greater than the first cross-sectional area. The second cross-sectional area is greater than a cross-sectional area of the proximal end of the passage when the expandable portion is in the expanded condition. A retaining mechanism resists movement of the expandable portion from the expanded condition toward the contracted condition.

The structure may also have a locking mechanism configured to prevent movement of the expandable portion from a predetermined condition toward one of the contracted condition and the expanded condition. In an exemplary embodiment, the locking mechanism may be located adjacent said expandable portion. The locking mechanism may include a guide member engageable with a stop defining a stop portion of a slot in the expandable portion.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is an exploded perspective view of a surgical cannula or structure constructed in accordance with a first embodiment of the present invention, the cannula being shown in an expanded condition;

FIG. 2 is a perspective view of the cannula of FIG. 1, the cannula being shown in a contracted condition;

DESCRIPTION OF THE INVENTION

Figure 3:
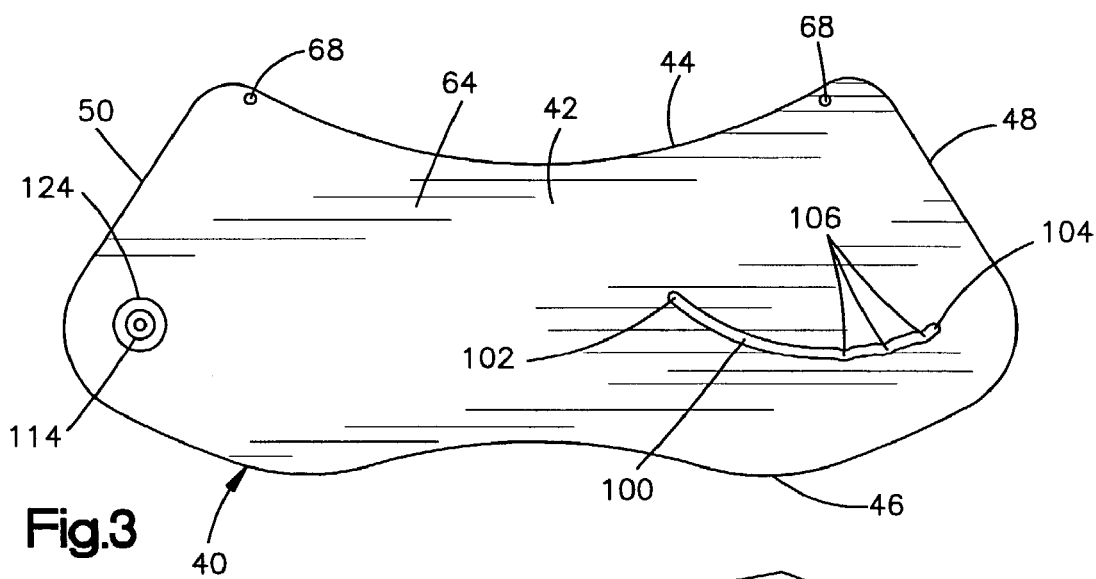
FIG. 3 is a rollout view of an arcuate segment of the cannula of FIG. 1.

The present invention is directed to a cannula or structure for receiving surgical instruments during a surgical procedure. The present invention is applicable to a variety of surgical procedures in which endoscopic, percutaneous, or minimally invasive surgical techniques are used.

FIG. 1 illustrates a cannula 10 constructed according to a first embodiment of the present invention. The cannula 10 may be a tubular structure 12 centered on an axis 14. Alternatively, the cannula 10 may be any other conduit or elongated structure which defines a passage therethrough. In the exemplary embodiment, the tubular structure 12 defines a passage 16 through the cannula 10. Surgical instruments are inserted into the body during surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material, such as a radiolucent material. The first tubular portion 20 has a proximal end 22 and a distal end 24. Parallel cylindrical inner and outer surfaces 26 and 28 extend between the ends 22, 24 of the first tubular portion 20. The first tubular portion 20 has a thickness measured perpendicular to the surfaces 26 and 28 in the range of 0.02 inches to 0.04 inches or approximately 0.5 mm to approximately 1.0 mm. It is contemplated that the tubular portion 20 could have any desired thickness.

The inner surface 26 (FIG. 1) defines a first passage portion 30 of the passage 16 through the cannula 10. The first passage portion 30 has a diameter D1 which is preferably in the range from 10 mm to 30 mm or approximately 0.4 inches to approximately 1.2 inches. It is contemplated that the first passage portion 30 could have any desired diameter. The inner surface 26 may have a non-reflective coating to reduce glare on any video image produced by a video camera attached to an endoscope inserted through the passage 16.

The second tubular portion 40 of the tubular structure 12 is attached to the distal end 24 of the first tubular portion 20. The second tubular portion 40 is preferably made from stainless steel, but could alternatively be made from another suitable material, such as a radiolucent material.

As best seen in the rollout view of FIG. 3, the second tubular portion 40 includes an arcuate segment 42 of sheet stock. The arcuate segment 42 includes first and second edges 44 and 46. The arcuate segment 42 also includes first and second planar edges 48 and 50 extending between the edges 44 and 46. The first and second planar edges 48 and 50 are rolled in an overlapping manner to form the tubular configuration of the second tubular portion 40.

When the second tubular portion 40 (FIG. 1) has been rolled into its tubular configuration, the first and second edges 44 and 46 define oppositely disposed first and second ends 60 and 62 of the second tubular portion. The first and second ends 60 and 62 are connected by a central portion 64. The first end 60 of the second tubular portion 40 is attached to the distal end 24 of the first tubular portion 20 by a suitable fastener, such as a rivet 66. It is contemplated that a screw could be used instead of the rivet 66. The rivet 66 extends through two aligned apertures 68 at the first end 60 of the second tubular portion 40.

The rivet 66 has a first portion 70 and a second portion 72. The first portion 70 has a shaft 74 extending from a head 76. The shaft 74 extends through the apertures 68 in the tubular portion 40 and the head 76 engages the inner surface 26 of the first tubular portion 20. A cylindrical opening 78 extends through the shaft 74 and the head 76.

The second portion 72 of the rivet 66 has a shaft 80 extending from a head 82. The shaft 80 extends into the opening 78 in the first portion 68 of the rivet 66 and the head 82 engages the second tubular portion 40. The shaft 80 of the second portion 72 extends into the opening 78 in the first portion 70 to connect the first and second portions of the rivet 66 and pivotally connect the second tubular portion 40 to the first tubular portion 20.

The second tubular portion 40 (FIG. 1) includes parallel inner and outer surfaces 90 and 92 extending between the first and second ends 60 and 62. The inner surface 90 defines a second passage portion 94 of the passage 16 through the cannula 10 which extends as a continuation of the first passage portion 30 in the first tubular portion 20. The second tubular portion 40 has a thickness measured perpendicular to the surfaces 90 and 92 in the range of 0.003 inches to 0.007 inches or approximately 0.075 mm to approximately 0.175 mm. The second tubular portion 40 may have any desired thickness. The inner surface may have a non-reflective coating that reduces glare on any video image produced by a camera attached to an endoscope inserted through the passage 16.

An arcuate slot 100 (FIGS. 1 and 3) is formed in the second tubular portion 40 and extends between the inner and outer surfaces 90 and 92 of the second tubular portion. The arcuate slot 100 extends in a circumferential direction and along a curvilinear path in the central portion 64 of the second tubular portion 40 toward the end 62 of the second tubular portion. The arcuate slot 100 has a first end 102 located in the central portion 64 of the second tubular portion 40. A second end 104 of the arcuate slot 100 is located adjacent the intersection of the second edge 46 and the planar edge 48 of the arcuate segment 42.

Figure 4:
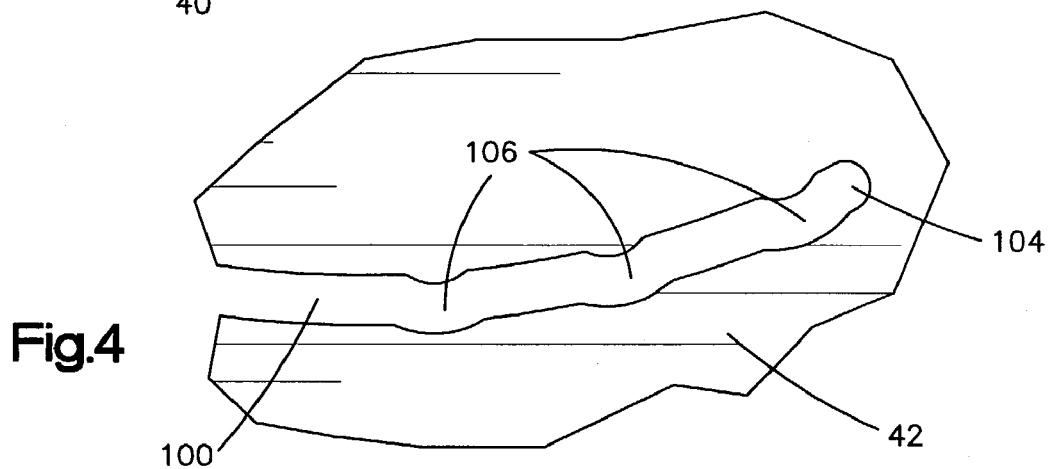
FIG. 4 is an enlarged view of a slot in the arcuate segment of FIG. 3.

The arcuate slot 100 (FIGS. 3 and 4) has three notches or stops 106 between the ends 102 and 104. The notches 106 define three expanded conditions of the second tubular portion 40. The notches 106 at least partially define a retaining mechanism for resisting movement of the second tubular portion 40 from the expanded conditions toward a contracted condition. The notches 106 extend in directions transverse to the circumferential direction in which the slot 100 extends. Although the present invention shows three stops 106, it is contemplated that the slot could have any number of stops.

A guide member or rivet 114 (FIGS. 1 and 3) is attached to the inner surface 90 of the second tubular portion 40 adjacent the intersection of the second edge 46 and the planar edge 50. It is contemplated that a guide pin or screw could be used instead of the rivet 114. In the tubular configuration of the second tubular portion 40, the guide member 114 is located in the arcuate slot 100 and is movable along the curvilinear path of the arcuate slot.

The rivet 114 (FIG. 1) is generally similar to the rivet 66 and, therefore, will not be described in detail. The rivet 114 has a first portion 116 and a second portion 118. The first portion 116 has a shaft 120 extending from a head 122. The shaft 120 extends through the slot 100 and the head 122 engages a washer 124. A cylindrical opening 126 extends through the shaft 120 and the head 122.

The second portion 118 of the rivet 114 has a shaft 128 extending from a head 130. The shaft 128 extends into the opening 126 in the first portion 116 of the rivet 114 and the head 130 engages the outer surface 92 of the second tubular portion 40. The shaft 120 extends into the opening 126 to connect the first portion 116 of the rivet 114 to the second portion 118.

The second tubular portion 40 of the tubular structure 12 is expandable from a contracted condition, shown in FIG. 2, to any one of three expanded conditions, one of which is shown in FIG. 1. In the contracted condition, the guide member 114 is located in the first end 102 of the arcuate slot 100 in the second tubular portion 40. The second passage portion 94 defined by the second tubular portion 40 is cylindrical in shape. The second passage portion 94 has a generally constant diameter D2 which is approximately equal to the diameter D1 of the first tubular portion 20. Thus, the cross-sectional area of the second passage portion 94 at the second end 62 of the second tubular portion 40 is approximately the same as the cross-sectional area at the first end 60 of the second tubular portion and is approximately the same as the cross-sectional area of the first passage portion 30 in the first tubular portion 20.

In the expanded conditions (FIG. 1), the guide member 114 engages one of the stops 106 and is located in one of the notches 106 in the arcuate slot 100 in the second tubular portion 40. It is also contemplated that the guide member 114 could engage one of the stops 106 and be located between adjacent notches 106. The stops 106 retain the guide member 114 in one of a plurality of positions relative to the slot 100 and resist movement of the guide member from one of the plurality of positions relative to the slot. Accordingly, the stops 106 resist contraction of the second tubular portion 40.

Figure 5:
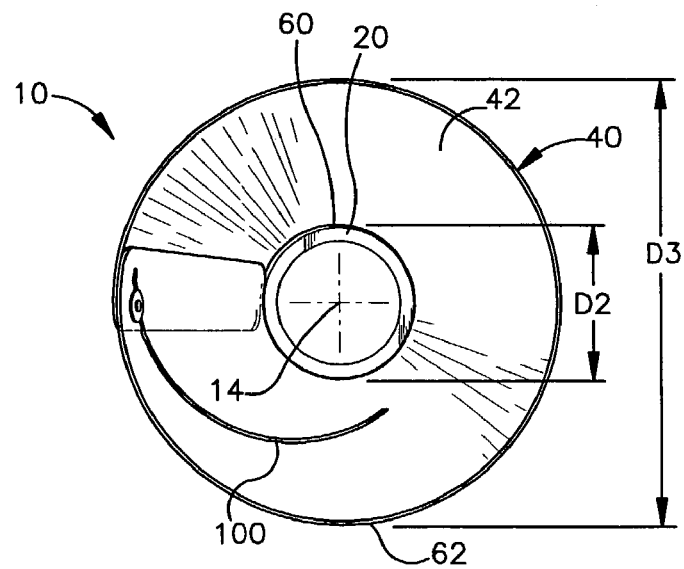
FIG. 5 is a schematic end view showing the cannula of FIG. 1 in the expanded condition.

The second tubular portion 40 has a conical configuration when in the expanded conditions. The configuration of the second tubular portion 40 when inside the body of a patient will vary depending on the forces exerted by surrounding tissue on the second tubular portion. At the second end 62 (FIG. 5) of the second tubular portion 40, the second passage portion 94 has a diameter D3 which is larger than the diameter D2 of the second passage portion at the first end 60. Thus, in the expanded conditions, the cross-sectional area of the second passage portion 94 at the second end 62 of the second tubular portion 40 is greater than the cross-sectional area of the second passage portion at the first end 60 of the second tubular portion.

The cannula 10 (FIGS. 1 and 2) may include an outer member (not shown) for maintaining the second tubular portion 40 of the cannula in the contracted condition. It is contemplated that other suitable means for maintaining the second tubular portion 40 in the contracted condition could be employed. The outer member may be a layer of plastic tubing which is heat shrunk over both the first and second tubular portions 20 and 40 to hold the second tubular portion in the contracted condition. In addition, a loop of nylon string (not shown) for tearing the heat shrink tubing is wrapped around the heat shrink tubing so that it extends both underneath and on top of the tubing. An outer end of the string extends beyond the tubing.

Figure 6:
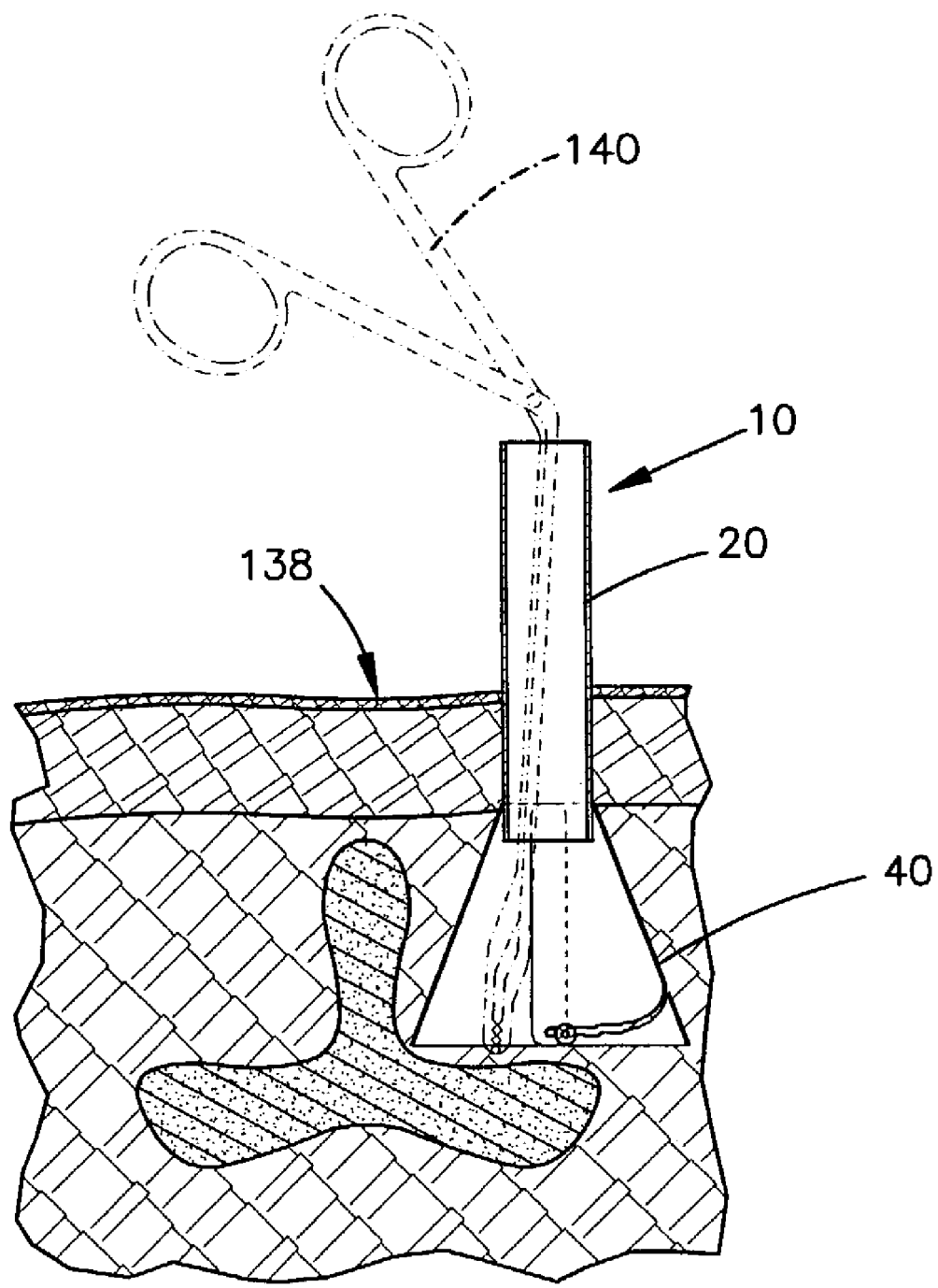
FIG. 6 is a schematic sectional view of the cannula of FIG. 1 adjacent a vertebrae of a patient's spine during a surgical procedure.

During a surgical procedure, the cannula 10 (FIG. 6) is inserted over a dilator, as known in the art, and through an incision into a body 138 of a patient in the contracted condition. The second tubular portion 40 is inserted inside the body 138. The first tubular portion 20 is inserted into the incision so that the first tubular portion extends from an exterior of the body 138 to inside the body.

The outer end of the string is then manually pulled on by the surgeon. Pulling on the string tears the heat shrink tubing. The heat shrink tubing remains on the cannula 10. With the heat shrink tubing torn, the second tubular portion 40 of the cannula 10 is thereby released for expansion toward one of the expanded conditions.

Next, an expansion tool (not shown) is inserted into the passage 16 in the cannula 10. The expansion tool is manually operated, causing a radially outwardly directed force to be exerted on the inner surface 90 of the second tubular portion 40 by the tool. The second tubular portion 40 expands toward one of the expanded conditions. Under the force of the expansion tool, the guide member 114 slides from the first end 102 of the arcuate slot 100 toward the second end 102 of the arcuate slot to permit the expansion of the second tubular portion 40. The guide member 114 engages a first stop 106 to position the guide member relative to the slot 100. If the second tubular portion 40 needs to be expanded further, additional force is applied to the second tubular portion to move the guide member 114. Expansion of the second tubular portion 40 can be stopped when the guide member 114 engages one of the stops 106. The guide member 114 engages the stops 106 to position the guide member in any one of the plurality of positions relative to the slot 100. The stops 106 resist movement of the guide member 114 relative to the slot 100. Accordingly, the second tubular portion 40 has a plurality of expanded conditions. The expansion tool is then removed so that one or more surgical instruments (indicated schematically at 140 in FIG. 6) can be received through the cannula 10 and inserted into a patient's body 138.

The expandable second tubular portion 40 of the cannula 10 provides a large working area for the surgeon inside the body 140 within the confines of the cannula. Furthermore, the second tubular portion 40 provides a working area that is only as large as needed. As a result, the simultaneous use of a number of surgical instruments, including but not limited to steerable instruments, shavers, dissectors, scissors, forceps, retractors, dilators, endoscopes, screwdrivers, distractors, burrs, kerrisons, and rongeurs, is made possible by the expandable cannula 10.

Figure 7:
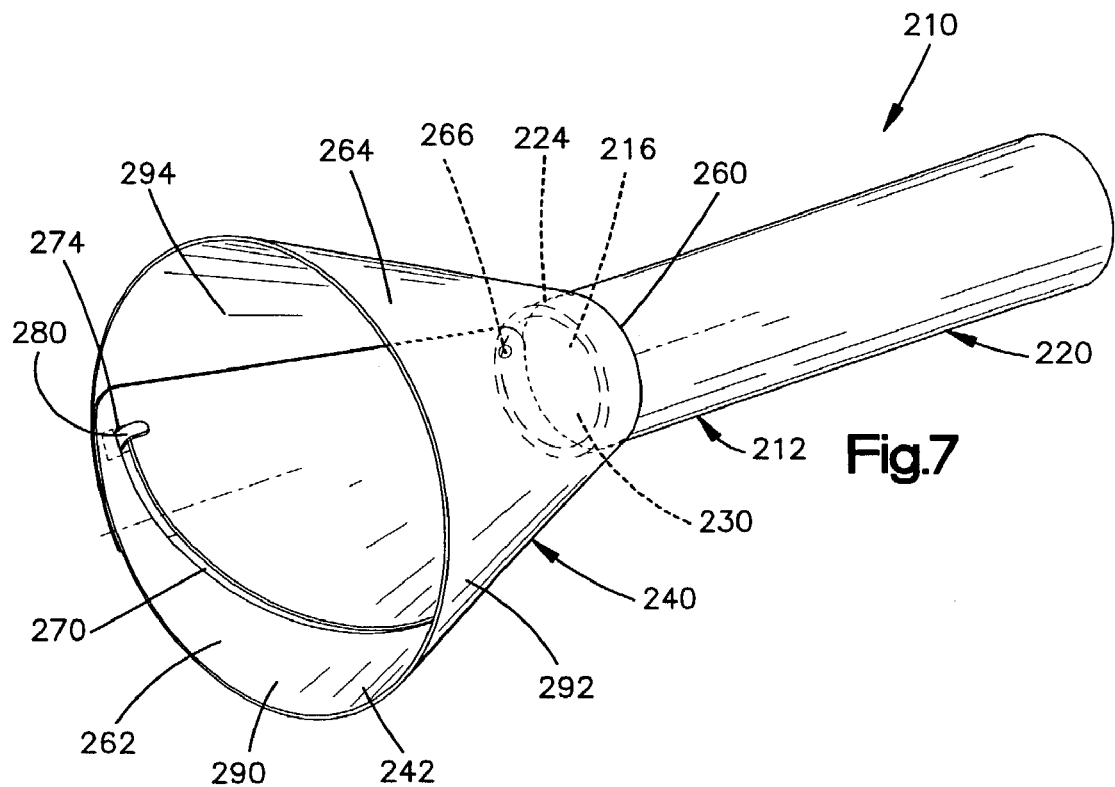
FIG. 7 is a schematic perspective view of a surgical cannula or structure constructed in accordance with a second embodiment of the present invention, the cannula being shown in an expanded condition.
Figure 8:
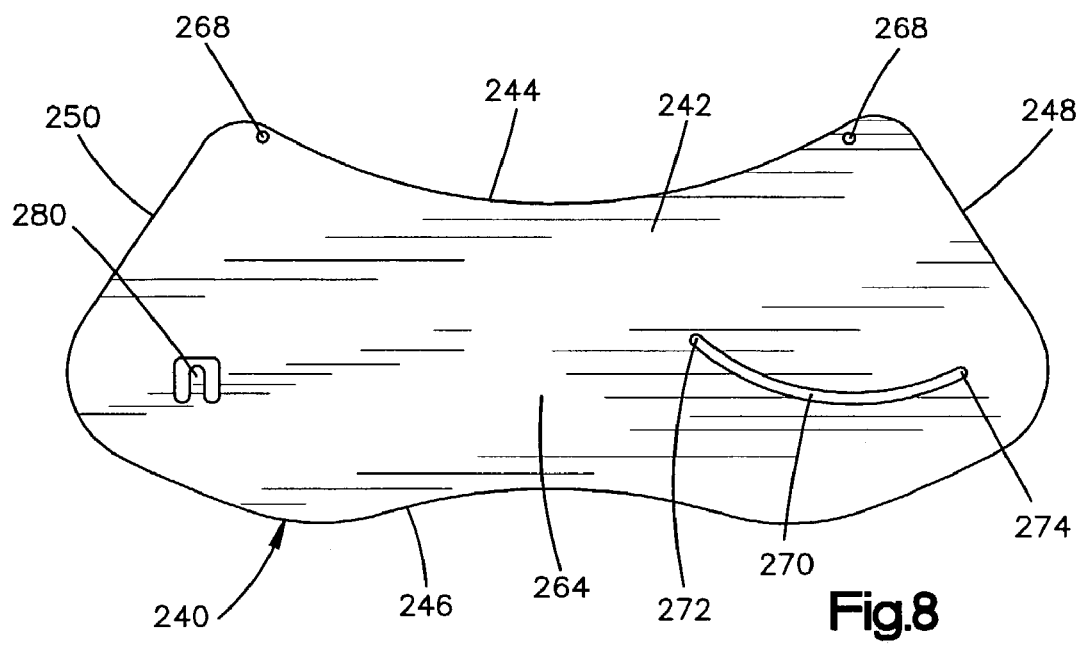
FIG. 8 is a rollout view of an arcuate segment of the cannula of FIG. 7.

A cannula or structure 210 constructed according to a second embodiment of the present invention is illustrated in FIGS. 7–8. The cannula 210 includes a tubular structure 212. The tubular structure 212 defines a passage 216 through the cannula 210. Surgical instruments are inserted into the body during surgery through the passage 216.

The tubular structure 212 comprises a first tubular portion 220 and a second tubular portion 240 attached to the first tubular portion. The first tubular portion 220 is identical to the first tubular portion 20 described in connection with the embodiment disclosed in FIGS. 1–6. Accordingly, the first tubular portion 220 will not be described in detail.

The second tubular portion 240 of the tubular structure 212 is attached to a distal end 224 of the first tubular portion 220. As best seen in the rollout view of FIG. 8, the second tubular portion 240 includes an arcuate segment 242 of sheet stock. The arcuate segment 242 includes first and second edges 244 and 246. The arcuate segment 242 also includes first and second planar edges 248 and 250 extending between the edges 244 and 246. The first and second planar edges 248 and 250 are rolled in an overlapping manner to form the tubular configuration of the second tubular portion 240.

When the second tubular portion 240 has been rolled into its tubular configuration, the first and second arcuate edges 244 and 246 define oppositely disposed first and second ends 260 and 262 (FIG. 7) of the second tubular portion. The first and second ends 260 and 262 are connected by a central portion 264. The first end 260 of the second tubular portion 240 is attached to the distal end 224 of the first tubular portion 220 by a suitable fastener, such as a rivet 266. The rivet 266 extends through two aligned apertures 268 (FIG. 8) at the first end 260 of the second tubular portion 240. The rivet 266 is identical to the rivet 66 described in connection with the embodiment illustrated in FIGS. 1–6. Accordingly, the rivet 266 will not be described in detail. It is contemplated that a screw could be used instead of the rivet 266.

The second tubular portion 240 (FIG. 7) includes parallel inner and outer surfaces 290 and 292 extending between the first and second ends 260 and 262. The inner surface 290 defines a second passage portion 294 of the passage 216 through the cannula 210 which extends as a continuation of a first passage portion 230 in the first tubular portion 220.

An arcuate slot 270 (FIGS. 7 and 8) is formed in the second tubular portion 240 and extends between the inner and outer surfaces 290 and 292 of the second tubular portion. The arcuate slot 270 extends in a circumferential direction and along a curvilinear path in the central portion 264 of the second tubular portion 240 toward the end 262 of the second tubular portion. The arcuate slot 270 has a first end 272 located in the central portion 264 of the second tubular portion 240. A second end 274 of the arcuate slot 270 is located adjacent the intersection of the second edge 246 and the planar edge 248 of the arcuate segment 242.

A guide member or tab 280 extends from the second tubular portion 240 at a location adjacent the intersection of the second edge 246 and the planar edge 250 of the arcuate segment 242. The tab 280 is formed by bending a cut-out of the arcuate segment 242 to extend through the slot 270. In the tubular configuration of the second tubular portion 240, the tab 280 is located in the arcuate slot 270 and is movable along the curvilinear path of the arcuate slot.

The second tubular portion 240 of the tubular structure 212 is expandable from a contracted condition to an expanded condition. In the contracted condition, the guide member 280 is located in the first end 272 of the arcuate slot 270 in the second tubular portion 240. The second passage portion 294 defined by the second tubular portion 240 is cylindrical in shape. The second passage portion 294 has a generally constant diameter which is approximately equal to the diameter of the first tubular portion 220. Thus, the cross-sectional area of the second passage portion 294 at the second end 262 of the second tubular portion 240 is approximately the same as a cross-sectional area at the first end 260 of the second tubular portion and is approximately the same as a cross-sectional area of the first passage portion 230 in the first tubular portion 220.

In the expanded condition, the guide member 280 is located in the second end 274 of the arcuate slot 270 in the second tubular portion 240. The second tubular portion 240 has a conical configuration. The configuration of the second tubular portion 240 when inside the body of a patient will vary depending on the forces exerted by surrounding tissue on the second tubular portion. At the second end 262 of the second tubular portion 240, the second passage portion 294 has a diameter which is larger than the diameter of the second passage portion at the first end 260. Thus, in the expanded condition, the cross-sectional area of the second passage portion 294 at the second end 262 of the second tubular portion 240 is greater than the cross-sectional area of the second passage portion at the first end 260 of the second tubular portion.

During a surgical procedure, the cannula 210 is inserted over a dilator and through an incision into the body of a patient in the contracted condition. The second tubular portion 240 is inserted inside the body. The first tubular portion 220 is inserted into the incision so that the first tubular portion extends from an exterior of the body to inside the body. A member, such as heat shrunk tubing, holding the second tubular portion 240 in the contracted condition is torn after insertion of the cannula 210.

An expansion tool (not shown) is inserted into the passage 216 in the cannula 210. The expansion tool is manually operated, causing a radially outwardly directed force to be exerted on the inner surface 290 of the second tubular portion 240 by the tool. The second tubular portion 240 expands toward the expanded condition. Under the force of the expansion tool, the guide member 280 slides from the first end 272 of the arcuate slot 270 to the second end 274 of the arcuate slot to permit the expansion of the second tubular portion 240. The expansion tool is then removed so that one or more surgical instruments can be received through the cannula 210 and inserted into a patient's body.

The expandable second tubular portion 240 of the cannula 210 provides a large working area for the surgeon inside the body within the confines of the cannula. As a result, simultaneous use of a number of surgical instruments, including but not limited to steerable instruments, shavers, dissectors, scissors, forceps, retractors, dilators, endoscopes, screwdrivers, distractors, burrs, kerrisons, and rongeurs, is made possible by the expandable cannula 210.

Figure 9:
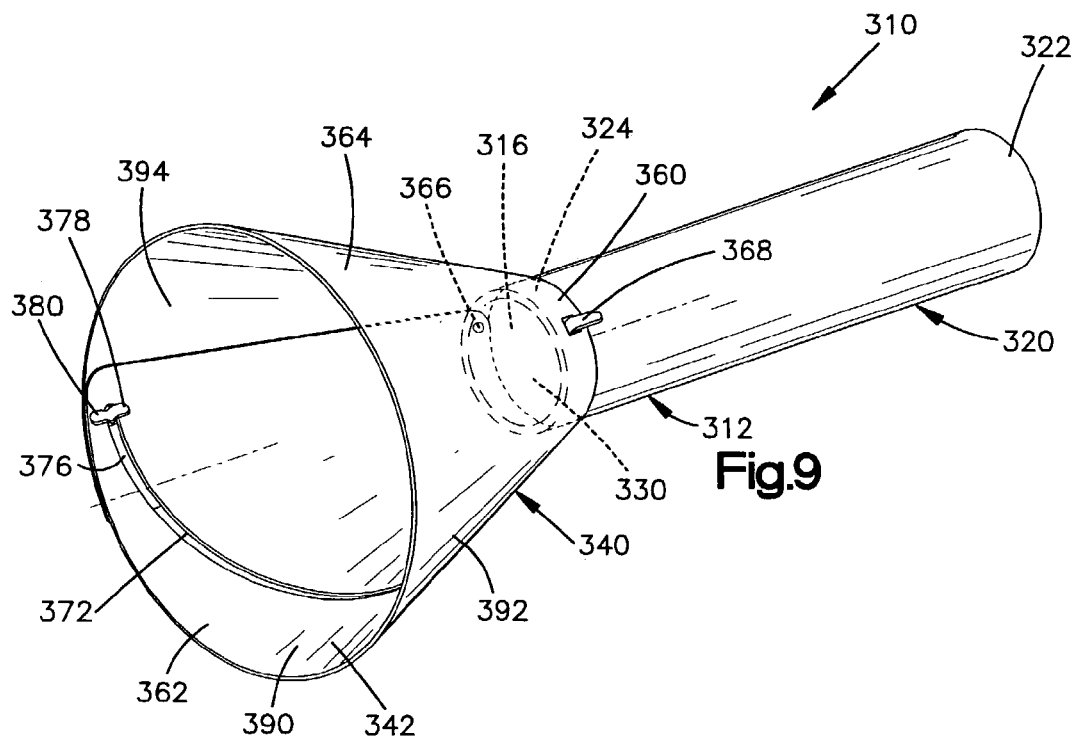
FIG. 9 is a schematic perspective view of a surgical cannula or structure constructed in accordance with a third embodiment of the present invention, the cannula being shown in an expanded condition.
Figure 10:
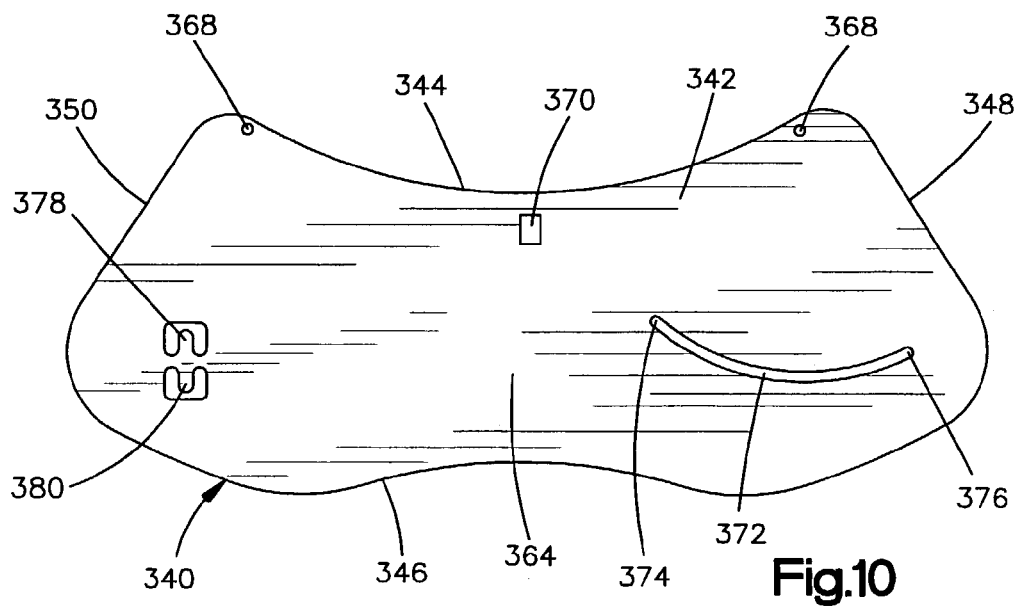
FIG. 10 is a rollout view of an arcuate segment of the cannula of FIG. 9.

A cannula or structure 310 constructed according to a third embodiment of the present invention is illustrated in FIGS. 9–10. The cannula 310 includes a tubular structure 312. The tubular structure 312 defines a passage 316 through the cannula 310. Surgical instruments are inserted into the body during surgery through the passage 316.

The tubular structure 312 comprises a first tubular portion 320 and a second tubular portion 340 attached to the first tubular portion. The first tubular portion 320 has a proximal end 322 and a distal end 324. Parallel cylindrical inner and outer surfaces extend between the ends 322 and 324 of the first tubular portion 320. The inner surface defines a first passage portion 330 of the passage 316 through the cannula 310.

The second tubular portion 340 of the tubular structure 312 is attached to the distal end 324 of the first tubular portion 320. As best seen in the rollout view of FIG. 10, the second tubular portion 340 includes an arcuate segment 342 of sheet stock. The arcuate segment 342 includes first and second edges 344 and 346. The arcuate segment 342 also includes first and second planar edges 348 and 350 extending between the edges 344 and 346. The first and second planar edges 348 and 350 are rolled in an overlapping manner to form the tubular configuration of the second tubular portion 340.

When the second tubular portion 340 (FIG. 9) has been rolled into its tubular configuration, the first and second edges 344 and 346 define oppositely disposed first and second ends 360 and 362 of the second tubular portion. The first and second ends 360 and 362 are connected by a central portion 364. The first end 360 of the second tubular portion 340 is attached to the distal end 324 of the first tubular portion 320 by a suitable fastener, such a rivet 366. The rivet 366 is identical to the rivet 66 described in connection with the embodiment illustrated in FIGS. 1–6. Accordingly, the rivet 366 will not be described in detail. The rivet 366 extends through aligned apertures 368 (FIG. 10) at the first end 360 of the second tubular portion 340. It is contemplated that a screw could be used instead of the rivet 366.

The first end 360 (FIGS. 9 and 10) of the second tubular portion 340 is also attached to the distal end 324 of the first tubular portion 320 by a tab 368 extending from the distal end 324 of the first tubular portion 320. The tab 368 extends through an opening 370 in the second tubular portion 340 and is bent over to connect the second tubular portion to the first tubular portion 320. The end of the tab 368 extending through the opening 370 may also be spot welded, soldered, or braized to the first tubular portion 320.

The second tubular portion 340 includes parallel inner and outer surfaces 390 and 392 extending between the first and second ends 360 and 362. The inner surface 390 defines a second passage portion 394 of the passage 316 through the cannula 310 which extends as a continuation of the first passage portion 330 in the first tubular portion 320.

An arcuate slot 372 is formed in the second tubular portion 340 and extends between the inner and outer surfaces 390 and 392 of the second tubular portion. The arcuate slot 372 extends in a circumferential direction and along a curvilinear path in the central portion 364 of the second tubular portion 340 toward the end 362 of the second tubular portion. The arcuate slot 372 has a first end 374 located in the central portion 364 of the second tubular portion 340. A second end 376 of the arcuate slot 372 is located adjacent the intersection of the second edge 346 and the planar edge 348 of the arcuate segment 342.

Guide members or tabs 378 and 380 extend from the second tubular portion 340 adjacent the intersection of the second edge 346 and the planar edge 350 of the arcuate segment 342. The tabs 378 and 380 are formed by bending cut-outs of the arcuate segment 342 to extend through the slot 370. In the tubular configuration of the second tubular portion 340, the tabs 378 and 380 are located in the arcuate slot 372 and are movable along the curvilinear path of the arcuate slot.

The second tubular portion 340 of the tubular structure 312 is expandable from a contracted condition to an expanded condition. In the contracted condition, the tabs 378 and 380 are located in the first end 374 of the arcuate slot 372 in the second tubular portion 340. The second passage portion 394 defined by the second tubular portion 340 is cylindrical in shape. The second passage 394 has a generally constant diameter which is approximately equal to the diameter of the first tubular portion 320. Thus, the cross-sectional area of the second passage portion 394 at the second end 362 of the second tubular portion 340 is approximately the same as the cross-sectional area at the first end 360 of the second tubular portion and is approximately the same as the cross-sectional area of the first passage portion 330 in the first tubular portion 320.

In the expanded condition, the tabs 378 and 380 are located in the second end 376 of the arcuate slot 372 in the second tubular portion 340. The second tubular portion 340 has a conical configuration. The configuration of the second tubular portion 340 when inside the body of a patient will vary depending on the forces exerted by surrounding tissue on the second tubular portion. At the second end 362 of the second tubular portion 340, the second passage portion 394 has a diameter which is larger than the diameter of the second passage portion at the first end 360. Thus, in the expanded condition, the cross-sectional area of the second passage portion 394 at the second end 362 of the second tubular portion 340 is greater than the cross-sectional area of the second passage portion at the first end 360 of the second tubular portion.

During a surgical procedure, the cannula 310 is inserted through an incision into the body of a patient in the contracted condition. The second tubular portion 340 is inserted inside the body. The first tubular portion 320 is inserted into the incision so that the first tubular portion extends from an exterior of the body to inside the body. A member, such as heat shrunk tubing, holding the second tubular portion in the contracted condition is torn after insertion of the cannula 310.

An expansion tool (not shown) is inserted into the passage 316 in the cannula 310. The expansion tool is manually operated, causing a radially outwardly directed force to be exerted on the inner surface 390 of the second tubular portion 340 by the tool. The second tubular portion 340 expands toward the expanded condition. Under the force of the expansion tool, the tabs 378 and 380 slide from the first end 374 of the arcuate slot 372 to the second end 376 of the arcuate slot to permit the expansion of the second tubular portion 340.

The expandable second tubular portion 340 of the cannula 310 provides a large working area for the surgeon inside the body within the confines of the cannula. As a result, the simultaneous use of a number of surgical instruments is made possible by the expandable cannula 310.

Figure 11:
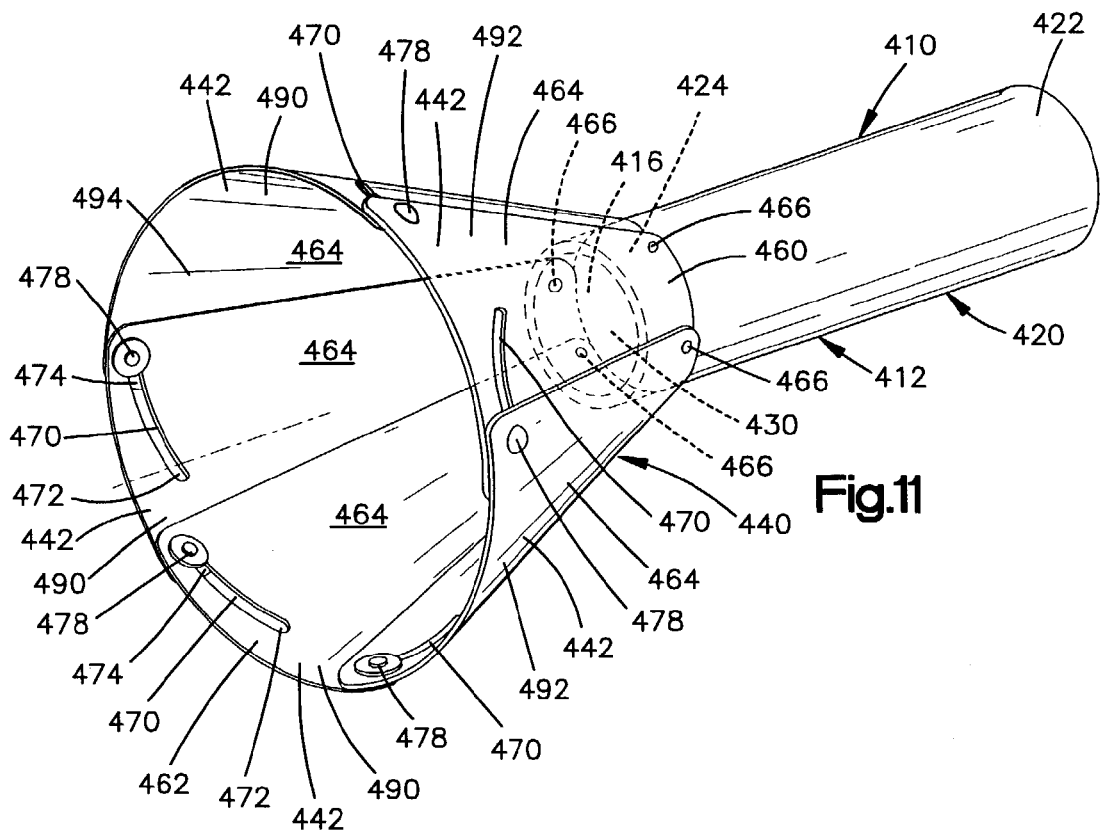
FIG. 11 is a schematic perspective view of a surgical cannula or structure constructed in accordance with a fourth embodiment of the present invention, the cannula being shown in an expanded condition.
Figure 12:
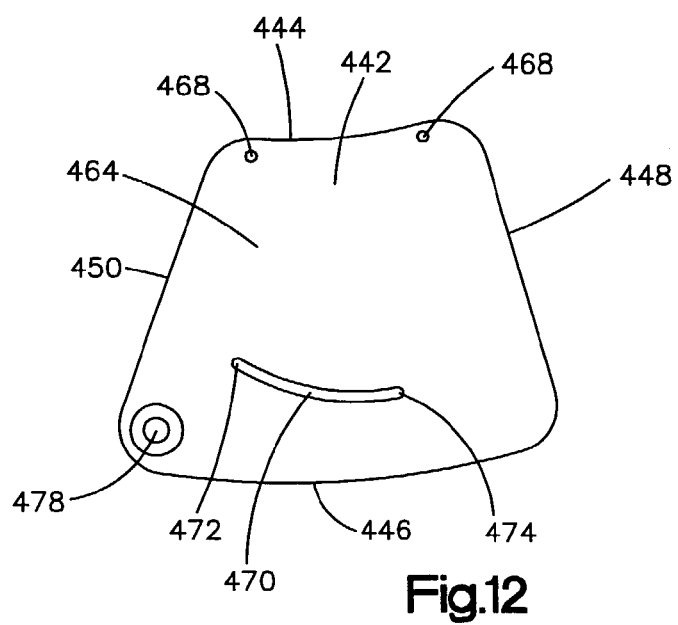
FIG. 12 is an enlarged rollout view of an arcuate segment of the cannula of FIG. 11.

A cannula or structure 410 constructed according to a fourth embodiment of the present invention is illustrated in FIGS. 11–12. The cannula 410 includes a tubular structure 412. The tubular structure 412 defines a passage 416 through the cannula 410. Surgical instruments are inserted into the body during surgery through the passage 416.

The tubular structure 412 comprises a first tubular portion 420 and a second tubular portion 440 attached to the first tubular portion. The first tubular portion 420 has a proximal end 422 and a distal end 424. Parallel cylindrical inner and outer surfaces extend between the ends 422 and 424 of the first tubular portion 420. The inner surface defines a first passage portion 430 of the passage 416 through the cannula 410.

The second tubular portion 440 of the tubular structure 412 is attached to the distal end 424 of the first tubular portion 420. The second tubular portion 440 includes a plurality of arcuate segments 442 of sheet stock. The present invention has five arcuate segments 442. However, it is contemplated that any number of arcuate segments 442 could be used.

The arcuate segments 442 are identical. Accordingly, only one of the arcuate segments 442 will be described in detail. The arcuate segment 442 (FIG. 12) includes first and second arcuate edges 444 and 446. The arcuate segment 442 also includes first and second planar edges 448 and 450 extending between the arcuate edges 444 and 446. The planar edges 448 and 450 of the arcuate segments 442 overlap each other to form the tubular configuration of the second tubular portion 440.

When the second tubular portion 440 (FIGS. 11–12) is in its tubular configuration, the arcuate edges 444 and 446 define oppositely disposed first and second ends 460 and 462 of the second tubular portion. The first and second ends 460 and 462 are connected by central portions 464 of the arcuate segments 442. The first end 460 of the second tubular portion 440 is attached to the distal end 424 of the first tubular portion 420 by suitable fasteners, such as rivets 466. The rivets 466 extend through aligned apertures 468 at the first end 460 of the second tubular portion 440. It is contemplated that screws could be used instead of the rivets 466.

Each of the arcuate segments 442 includes parallel inner and outer surfaces 490 and 492 extending between the first and second ends 460 and 462 of the second tubular portion 440. The inner surfaces 490 define a second passage portion 494 of the passage 416 through the cannula 410 which extends as a continuation of the first passage portion 430 in the first tubular portion 420.

Arcuate slots 470 are formed in the arcuate segments 442 and extend between the inner and outer surfaces 490 and 492 of the second tubular portion 440. The arcuate slots 470 extend in circumferential directions and along curvilinear paths in the central portions 464 of the arcuate segments 442 toward the end 462 of the second tubular portion. The arcuate slots 470 have first ends 472 located in the central portions 464. Second ends 474 of the arcuate slots 470 are located adjacent the end 462 of the second tubular portion 440. Guide members or rivets 478 are attached to the arcuate segments 442. The guide members 478 are identical to the guide member 114 described in connection with the embodiment illustrated in FIGS. 1–6. Accordingly, the guide members 478 will not be described in detail. It is contemplated that guide pins or screws could be used instead of the rivets 478. In the tubular configuration of the second tubular portion 440, the guide members 478 are located in the arcuate slots 470 and are movable along the curvilinear paths of the arcuate slots.

The second tubular portion 440 of the tubular structure 412 is expandable from a contracted condition to an expanded condition. In the contracted condition, the guide members 478 are located in the first ends 472 of the arcuate slots 470 in the second tubular portion 440. The second passage portion 494 defined by the second tubular portion 440 is cylindrical in shape. The second passage 494 has a generally constant diameter which is approximately equal to the diameter of the first tubular portion 420. Thus, the cross-sectional area of the second passage portion 494 at the second end 462 of the second tubular portion 440 is approximately the same as the cross-sectional area at the first end 460 of the second tubular portion and is approximately the same as the cross-sectional area of the first passage portion 430 in the first tubular portion 420.

In the expanded condition, the guide members 478 are located in the second ends 474 of the arcuate slots 470 in the second tubular portion 440. The second tubular portion 440 has a conical configuration. The configuration of the second tubular portion 440 when inside the body of a patient will vary depending on the forces exerted by surrounding tissue on the second tubular portion. At the second end 462 of the second tubular portion 440, the second passage portion 494 has a diameter which is larger than the diameter of the second passage portion at the first end 460. Thus, in the expanded condition, the cross-sectional area of the second passage portion 494 at the second end 462 of the second tubular portion 440 is greater than the cross-sectional area of the second passage portion at the first end 460 of the second tubular portion.

During a surgical procedure, the cannula 410 is inserted over a dilator and through an incision into the body of a patient in the contracted condition. The second tubular portion 440 is inserted inside the body. The first tubular portion 420 is inserted into the incision so that the first tubular portion extends from an exterior of the body to inside the body. A member, such as heat shrunk tubing, holding the second tubular portion 440 in the contracted condition is torn after insertion of the cannula 410.

An expansion tool (not shown) is inserted into the passage 416 in the cannula 410. The expansion tool is manually operated, causing a radially outwardly directed force to be exerted on the inner surfaces 490 of the second tubular portion 440 by the tool. The second tubular portion 440 expands toward the expanded condition. Under the force of the expansion tool, the guide members 478 slide from the first ends 472 of the arcuate slots 470 to the second ends 474 of the arcuate slots to permit the expansion of the second tubular portion 440.

The expandable second tubular portion 440 of the cannula 410 provides a large working area for the surgeon inside the body within the confines of the cannula. As a result, the simultaneous use of a number of surgical instruments is made possible by the expandable cannula 410. Although the slots 470 are shown as not having stops, it is contemplated that the slots could have stops or notches similar to the stops 106 described in connection with the embodiment illustrated in FIGS. 1–6.

Figure 13:
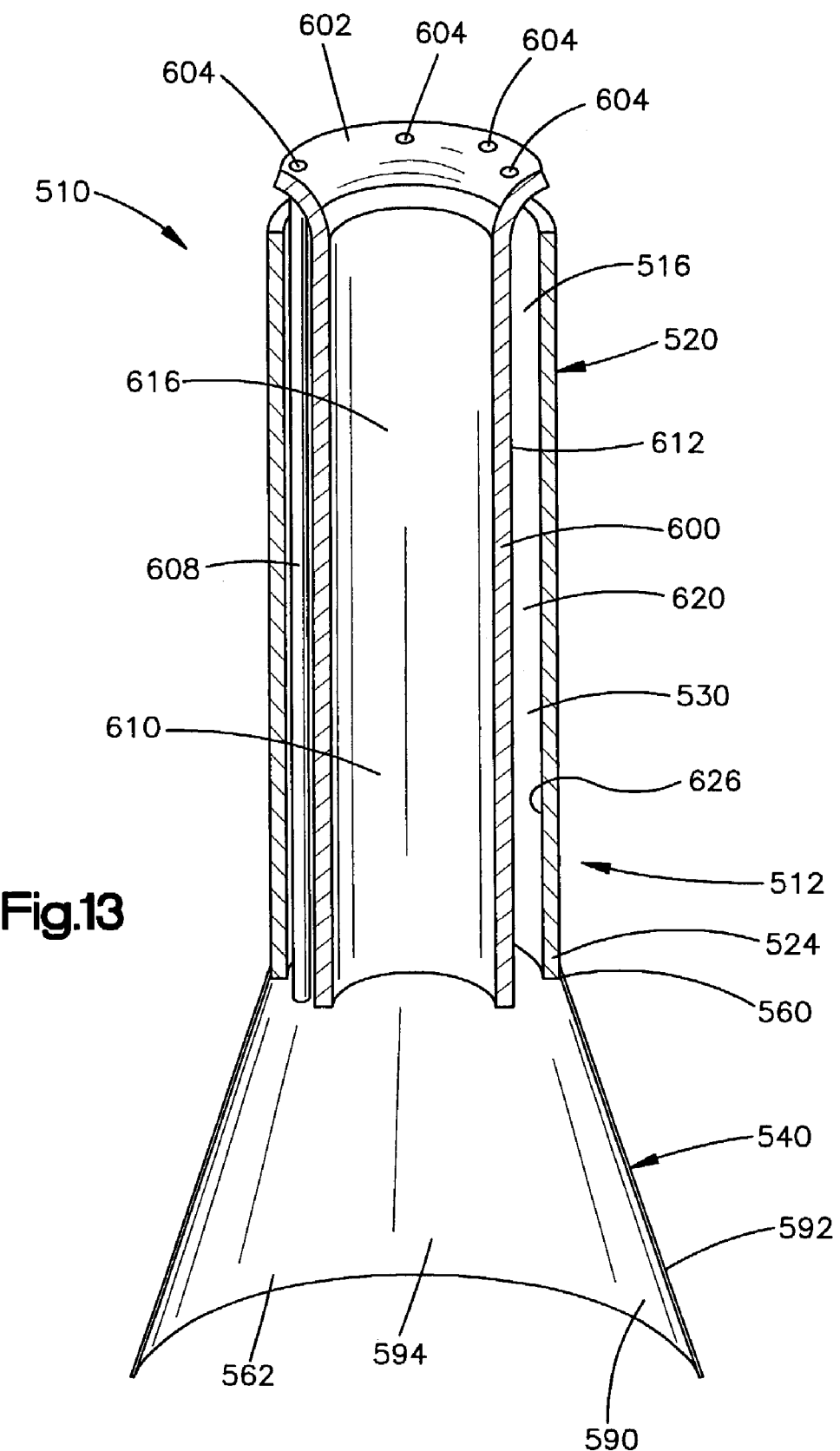
FIG. 13 is a schematic sectional view of a surgical cannula or structure constructed in accordance with a fifth embodiment of the present invention.

A cannula or structure 510 constructed according to a fifth embodiment of the present invention is illustrated in FIG. 13. The cannula 510 includes a tubular structure 512. The tubular structure 512 defines a passage 516 through the cannula 510. Surgical instruments are inserted into the body during surgery through the passage 516.

The tubular structure 512 comprises a first tubular portion 520 and a second tubular portion 540 attached to the first tubular portion. The first and second tubular portions 520 and 540 are identical to the first and second tubular portions 20 and 40 described in connection with the embodiment disclosed in FIGS. 1–6. Accordingly, the first and second tubular portions 520 and 540 will not be described in detail.

The second tubular portion 540 of the tubular structure 512 is attached to a distal end 524 of the first tubular portion 520. A first end 560 of the second tubular portion 540 is attached to the distal end 524 of the first tubular portion 520 by a suitable fastener (not shown), such as a rivet. The second tubular portion 540 includes parallel inner and outer surfaces 590 and 592 extending between first and second ends 560 and 562. The inner surface 590 defines a second passage portion 594 of the passage 516 through the cannula 510 which extends as a continuation of a first passage portion 530 in the first tubular portion 520.

The second tubular portion 540 of the tubular structure 512 is expandable from a contracted condition to an expanded condition. In the contracted condition, the second passage portion 594 defined by the second tubular portion 540 is cylindrical in shape. The second passage portion 594 has a generally constant diameter which is approximately equal to the diameter of the first tubular portion 520. Thus, the cross-sectional area of the second passage portion 594 at the second end 562 of the second tubular portion 540 is approximately the same as a cross-sectional area at the first end 560 of the second tubular portion and is approximately the same as a cross-sectional area of the first passage portion 530 in the first tubular portion 520.

In the expanded condition, the second tubular portion 540 has a conical configuration. The configuration of the second tubular portion 540 when inside the body of a patient will vary depending on the forces exerted by surrounding tissue. At the second end 562 of the second tubular portion 540, the second passage portion 594 has a diameter which is larger than the diameter of the second passage portion at the first end 560. Thus, in the expanded condition, the cross-sectional area of the second passage portion 594 at the second end 562 of the second tubular portion 540 is greater than the cross-sectional area of the second passage portion at the first end 560 of the second tubular portion.

A second tubular structure 600 extends into the first tubular portion 520 of the tubular structure 512. The second tubular portion 600 extends into the first passage portion 530. The second tubular structure 600 has a radially extending flange 602 with openings 604 for receiving surgical instruments and/or for application of suction or irrigation fluid. A tube 608 may extend from the flange 602 adjacent one of the openings 604 for receiving a surgical instrument and/or the application of suction or irrigation fluid.

The second tubular structure 600 includes parallel inner and outer surfaces 610 and 612. The inner surface 610 defines a passage 616 through the second tubular structure 600. The outer surface 612 and the inner surface 626 of the first tubular portion 520 define an annular passage 620. The openings 604 in the flange 602 of the second tubular structure 600 communicate with the annular passage 620. Accordingly, surgical instruments extend through the openings 604 into the annular passage 620.

During a surgical procedure, the cannula 510 is inserted over a dilator and through an incision into the body of a patient in the contracted condition. The second tubular portion 540 is inserted inside the body. The first tubular portion 520 is inserted into the incision so that the first tubular portion extends from an exterior of the body to inside the body. A member, such as heat shrunk tubing, holding the second tubular portion 540 in the contracted condition is torn after insertion of the cannula 510.

Next, an expansion tool (not shown) is inserted into the passage 516 in the cannula 510. The expansion tool is manually operated, causing a radially outwardly directed force to be exerted on the inner surface 590 of the second tubular portion 540 by the tool. The second tubular portion 540 expands toward the expanded condition. The expansion tool is then removed so that the second tubular structure 600 may be inserted into the passage 516.

The second tubular structure 600 is inserted into the passage 516 to define the annular passage 620. Surgical instruments can be received through the openings 604 in the flange 602 and into the annular passage 620 and one or more surgical instruments can be received through the passage 616 and/or suction or irrigation fluid can be applied through the passage 616. As a result, the simultaneous use of a number of surgical instruments is made possible by the cannula 510.

Figure 14:
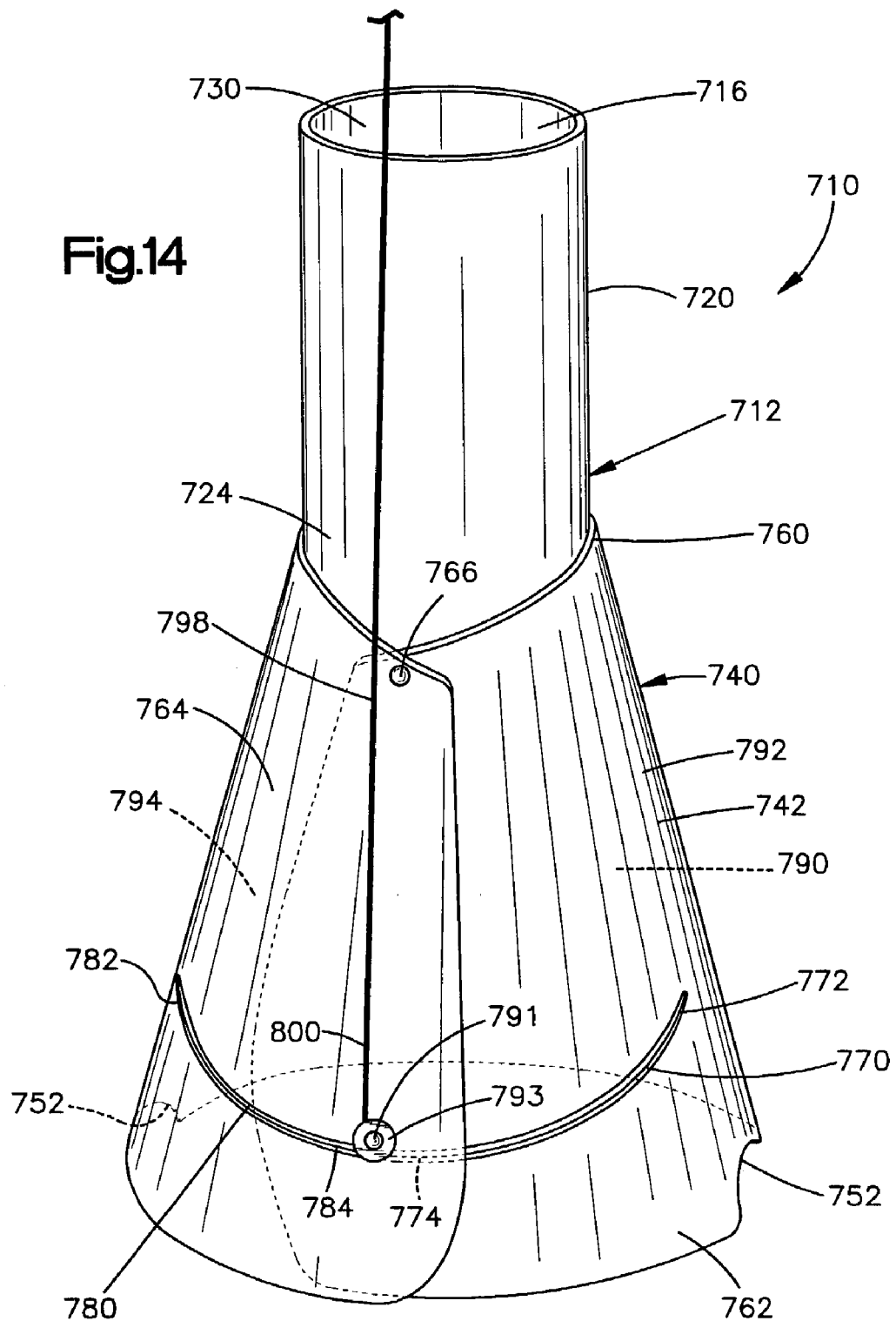
FIG. 14 is a schematic perspective view of a surgical cannula or structure constructed in accordance with a sixth embodiment of the present invention.
Figure 15:
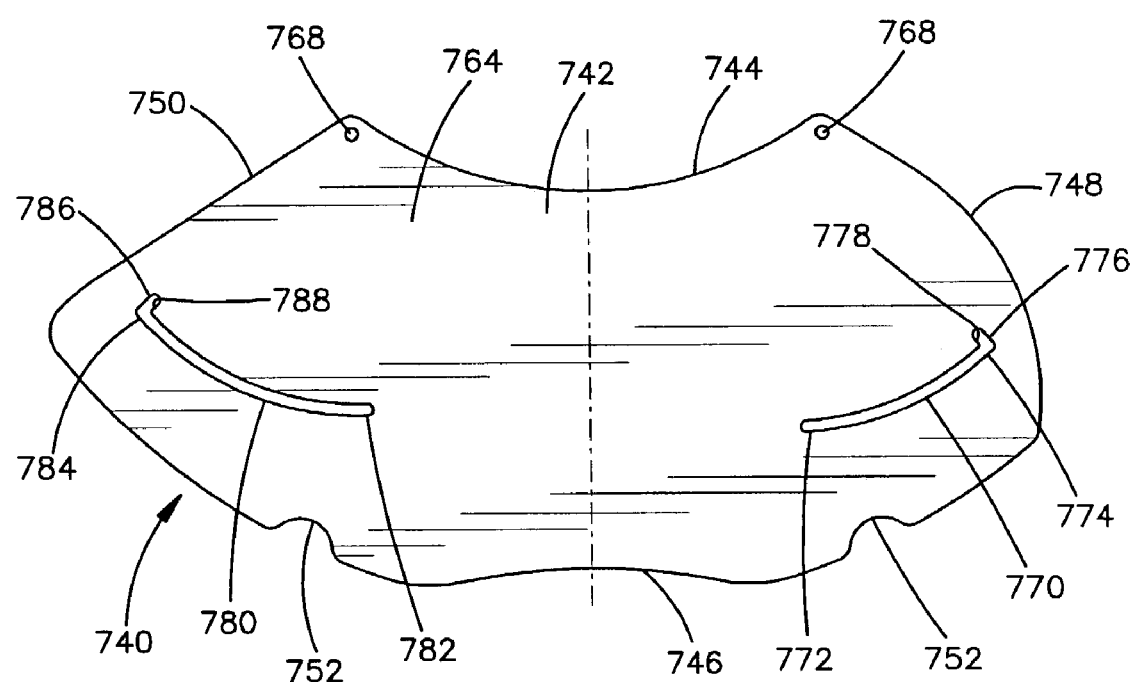
FIG. 15 is a rollout view of an embodiment of an arcuate segment of the cannula of FIG. 14.

A cannula or structure 710 constructed according to a sixth embodiment of the present invention is illustrated in FIGS. 14 and 15. The cannula 710 includes a tubular structure 712. The tubular structure 712 defines a passage 716 through the cannula 710. Surgical instruments are inserted into the body during a surgery through the passage 716.

The tubular structure 712 includes a first tubular portion 720 and a second tubular portion 740 attached to the first tubular portion. The first tubular portion 720 is identical to the first tubular portion 20 described in connection with the embodiment disclosed in FIGS. 1–6. Accordingly, the first tubular portion 720 will not be described in detail.

The second tubular portion 740 of the tubular structure 712 is attached to a distal end 724 of the first tubular portion 720. As best seen in the rollout view of FIG. 15, the second tubular portion 740 includes an arcuate segment 742 of sheet stock. The arcuate segment 742 includes upper and lower edges 744 and 746. The arcuate segment 742 also includes first and second edges 748 and 750 extending between the edges 744 and 746. The first and second edges 748 and 750 are rolled in an overlapping manner to form the tubular configuration of the second tubular portion 740. The lower edge 746 includes two semi-circular cut-outs 752. A spinal fixation element or rod may pass through the cut-outs 52 during a surgical procedure when the second tubular portion 740 is in an expanded condition.

When the second tubular portion 740 has been rolled into its tubular configuration, the upper and lower edges 744 and 746 define oppositely disposed first and second ends 760 and 762 (FIG. 14) of the second tubular portion. The first and second ends 760 and 762 are connected by a central portion 764. The first end 760 of the second tubular portion 740 is attached to the distal end 724 of the first tubular portion 720 by a suitable fastener, such as a rivet 766. The rivet 766 extends through two aligned apertures 768 (FIG. 15) at the first end 760 of the second tubular portion 740. The rivet 766 may have any desired configuration. It is also contemplated that a screw could be used instead of the rivet 766.

The second tubular portion 740 (FIG. 14) includes parallel inner and outer surfaces 790 and 792 extending between the first and second ends 760 and 762. The inner surface 790 defines a second passage portion 794 of the passage 716 through the cannula 710 which extends as a continuation of a first passage portion 730 in the first tubular portion 720.

A first slot 770 (FIGS. 14 and 15) is formed in the second tubular portion 740 and extends between the inner and outer surfaces 790 and 792 of the second tubular portion. The first slot 770 extends in a circumferential direction and along a curvilinear path in the central portion 764 of the second tubular portion 740 toward the end 762 of the second tubular portion. The first slot 770 has a first end 772 located in the central portion 764 of the second tubular portion 740. A second end 774 of the first slot 770 is located adjacent the intersection of the lower edge 746 and the first edge 748 of the arcuate segment 742.

The slot 770 (FIG. 15) includes a stop portion 776 extending in a proximal direction from the second end 774 of the slot. It is contemplated that the stop portion 776 may alternatively extend from an intermediate location on the slot 770. For example, the second tubular portion 740 may be initially expanded to the expanded condition, and subsequently retained or locked in a slightly smaller intermediate condition. The stop portion 776 extends transverse to the circumferential direction and defines a stop 778. The stop 778 defines a retaining mechanism for resisting movement of the second tubular portion 740 from the expanded condition toward a contracted condition.

A second slot 780 (FIGS. 14 and 15) is formed in the second tubular portion 740 and extends between the inner and outer surfaces 790 and 792 of the second tubular portion. The second slot 780 extends in a circumferential direction and along a curvilinear path in the central portion 764 of the second tubular portion 740 toward the end 762 of the second tubular portion. The second slot 780 has a first end 782 located in the central portion 764 of the second tubular portion 740. A second end 784 of the second slot 780 is located adjacent the intersection of the lower edge 746 and the second edge 750 of the arcuate segment 742.

The slot 780 includes a stop portion 786 extending in a proximal direction from the second end 784. The stop portion 786 extends transverse to the circumferential direction and defines a stop 788. The stop 788 defines the retaining mechanism for resisting movement of the second tubular portion 740 from the expanded condition toward the contracted condition.

A guide member or rivet 791 (FIG. 14) extends through the first and second slots 770 and 780 in the second tubular portion 740. The rivet 791 may have any desired configuration. It is also contemplated that a guide pin or screw could be used instead of the rivet 791. In the tubular configuration of the second tubular portion 740, the guide member 791 is located in the slots 770 and 780 and is movable along the curvilinear path of the slots.

The rivet 791 extends through two washers 793, one of which is shown in FIG. 14, and the slots 780 and 770. One of the washers 793 engages the inner surface 790 of the second tubular portion 740. The other washer 793 engages the outer surface 792 of the second tubular portion 740.

The second tubular portion 740 of the tubular structure 712 is expandable from the contracted condition to the expanded condition. In the contracted condition, the guide member 791 is located in the first ends 772 and 782 of the slots 770 and 780 in the second tubular portion 740. The second passage portion 794 defined by the second tubular portion 740 is cylindrical in shape. The second passage portion 794 has a generally constant diameter which is approximately equal to the diameter of the first tubular portion 720. Thus, the cross-sectional area of the second passage portion 794 at the second end 762 of the second tubular portion 740 is approximately the same as a cross-sectional area at the first end 760 of the second tubular portion and is approximately the same as a cross-sectional area of the first passage portion 730 in the first tubular portion 720.

In the expanded condition, the guide member 791 is located in the second ends 774 and 784 of the slots 770 and 780. The second tubular portion 740 has a conical configuration. The configuration of the second tubular portion 740 when inside the body of a patient will vary depending on the forces exerted by surrounding tissue. At the second end 762 of the second tubular portion 740, the second passage portion 794 has a diameter which is larger than the diameter of the second passage portion at the first end 760. Thus, in the expanded condition, a cross-sectional area of the second passage portion 794 at the second end 762 of the second tubular portion 740 is greater than the cross-sectional area of the second passage portion at the first end 760 of the second tubular portion.

The guide member 791 may be moved relative to the second tubular portion 740 from the second end portions 774 and 784 of the slots 770 and 780 into the stop portions 776 and 786 of the slots. The stops 778 and 788 engage the guide member 791 to resist movement of the second tubular portion 740 from the expanded condition toward the contracted condition.

According to another aspect of the present invention, the cannula, or structure, 710 is provided with a locking mechanism. As the term will be used herein, a locking mechanism is understood to refer to an arrangement of parts which prevents movement of the tubular portion 740 from a predetermined condition towards the contracted condition (or alternatively, toward the expanded condition). The predetermined condition is understood to refer to the expanded condition or any other desirable intermediate condition. Moreover, the predetermined condition may refer to a particular cross-sectional area, or alternatively, to a particular range of cross-sectional areas, as discussed below.

When engaged, the locking mechanism maintains the tubular portion 740 in the predetermined condition against forces which may be exerted by surrounding tissue to move the tubular portion 740 towards the contracted condition. In the exemplary embodiment, when guide member 791 is positioned within the substantially transversely-oriented stop portions 776 and 786, the stops 778 and 788 and guide member 791 function as a locking mechanism, e.g., stops 778 and 788 may engage the guide member 791 and thereby prevent movement of the guide member 791 in a circumferential direction. The range of motion available with respect to the predetermined condition is determined by the width of the stop portions 776 and 786. For example, if the width of the stop portions 776 and 786 is substantially the same as the dimension of the guide member 791, the locking mechanism maintains the tubular portion 740 in a substantially fixed configuration. Consequently, relative movement of the first and second edges 748 and 750 with respect to each other is substantially prevented. Alternatively, if stop portions 776 and 786 are wider than the guide member 791 in a circumferential direction, the tubular portion 740 may be able to move within a range of cross-sectional areas, and the first and second edges 748 and 750 are allowed a commensurate degree of relative movement.

The guide member 791 may be moved into the stop portions 776 and 786 of the slots 770 and 780 by a tether member 798. The tether member 798 is substantially rigid and may be made of any suitable material, such as Nitinol.

The tether member 798 has a first end 800 connected with the guide member 791. The tether member 800 may be connected with the guide member 791 in any suitable manner. It is contemplated that the tether member 798 may be formed as one piece with the washer 793 located on the outside of the second tubular portion 740. It is also contemplated that the tether member 798 may be connected with the second tubular portion 740 to move the second tubular portion relative to the guide member 791.

The tether member 798 extends from the guide member 791 along the length of the first and second tubular portions 720 and 740 along the outside of the cannula 710. The tether member 798 may be moved in a proximal direction relative to the cannula 710 to move the guide member 791 into the stop portions 776 and 786 of the slots 770 and 780. The tether member 798 may be moved in a distal direction relative to the cannula 710 to move the guide member 791 out of the stop portions 776 and 786 and into the second ends 774 and 784 to permit contraction of the second tubular portion 740.

It is contemplated that the tether member 798 may extend through the passage 716 in the cannula 710 and be connected to the guide member 791. It is also contemplated that the tether member 798 may be a suture or nylon string used to pull the guide member 791 into the stop portions 776 and 786 and a tool could be used to move the guide member from the stop portions. It is also contemplated that the tether member 798 may not be used. A tool could be inserted into the passage 716 to move the guide member 791 into the stop portions 776 and 786.

During a surgical procedure, the cannula 710 is inserted over a dilator and through an incision into the body of a patient in the contracted condition. The second tubular portion 740 is inserted inside the body. The first tubular portion 720 is inserted into the incision so that the first tubular portion extends from an exterior of the body to inside the body. A member, such as heat shrunk tubing, for maintaining the second tubular portion 740 in the contracted condition may also hold the tether member 798 adjacent the outer surface of the cannula 710 during insertion of the cannula. The member holding the second tubular portion 740 in the contracted condition is torn after insertion of the cannula.

An expansion tool (not shown) is inserted into the passage 716 in the cannula 710. The expansion tool is manually operated, causing a radially outwardly directed force to be exerted on the inner surface 790 of the second tubular portion 740 by the tool. The second tubular portion 740 expands toward the expanded condition. Under the force of the expansion tool, the guide member 791 slides from the first ends 772 and 782 of the slots 770 and 780 toward the second ends 774 and 784 of the slots to permit the expansion of the second tubular portion 740. The tether member 798 is moved proximally relative to the cannula 710 to move the guide member 791 into the stop portions 776 and 786 of the slots 770 and 780. The stops 778 and 788 on the second tubular portion 740 engage the guide member 791 to resist movement of the second tubular portion 740 from the expanded condition toward the contracted condition. The expansion tool is removed so that one or more surgical instruments can be received through the cannula 710 and inserted into a patient's body.

Upon conclusion of the surgical procedure, the tether member 798 is moved distally relative to the cannula 710. The tether member 798 moves the guide member 791 from the stop portions 776 and 786 of the slots 770 and 780 into the second ends 774 and 784. Accordingly, the second tubular portion 740 can move from the expanded condition into the contracted condition for removal of the cannula 710 from the body of the patient.

The expandable second tubular portion 740 of the cannula 710 provides a large working area for the surgeon inside the body within the confines of the cannula. As a result, simultaneous use of a number of surgical instruments, including but not limited to steerable instruments, shavers, dissectors, scissors, forceps, retractors, dilators, endoscopes, screwdrivers, distractors, burrs, kerrisons, and rongeurs, is made possible by the expandable cannula 710.

Figure 16:
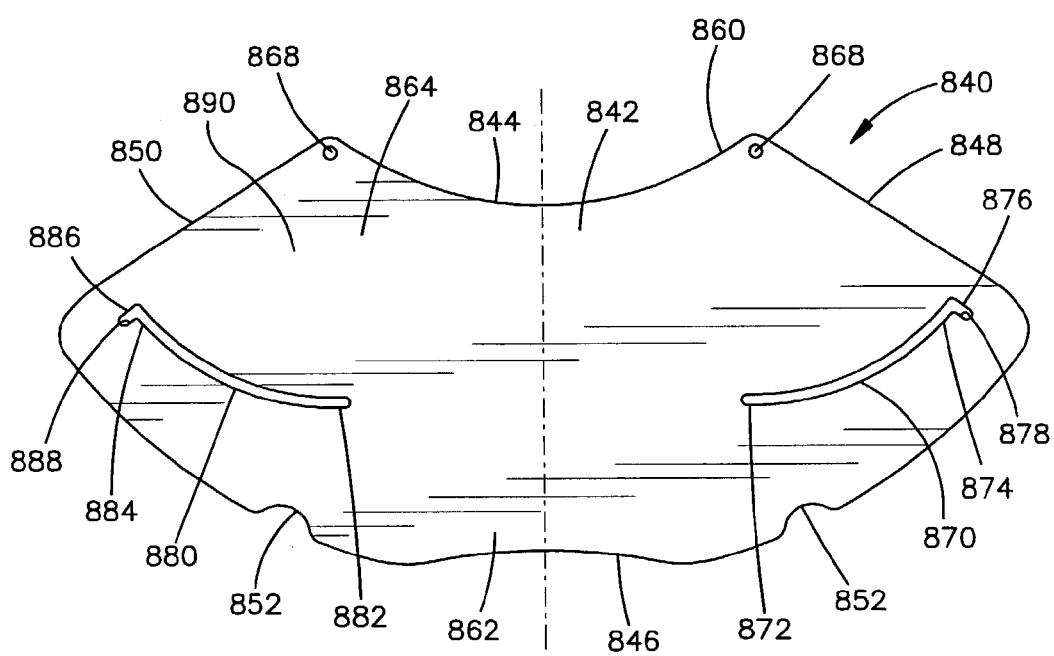
FIG. 16 is a rollout view of another embodiment of an arcuate segment of the cannula of FIG. 14.

Another embodiment of a second tubular portion for use with the first tubular portion 720 of the cannula 710, illustrated in FIG. 14, is illustrated in FIG. 16. A second tubular portion 840 includes an arcuate segment 842 of sheet stock. The arcuate segment 842 includes upper and lower edges 844 and 846. The arcuate segment 842 also includes first and second edges 848 and 850 extending between the edges 844 and 846. The first and second edges 848 and 850 are rolled in an overlapping manner to form the tubular configuration of a second tubular portion 840. The lower edge 846 includes two semi-circular cut-outs 852 through which a spinal fixation element may pass when the second tubular portion 840 is in an expanded condition.

When the second tubular portion 840 has been rolled into its tubular configuration, the upper and lower edges 844 and 846 define oppositely disposed first and second ends 860 and 862 of the second tubular portion. The first and second ends 860 and 862 are connected by a central portion 864. The first end 860 of the second tubular portion 840 is connected to the distal end 724 of the first tubular portion 720 by a suitable fastener, such as the rivet 766. The rivet 766 extends through two aligned apertures 868 at the first end 860 of the second tubular portion 840. It is also contemplated that a screw could be used instead of the rivet 766.

The second tubular portion 840 includes an inner surface 890 and a parallel outer surface extending between the first and second ends 860 and 862. The inner surface 890 defines a second passage portion of the passage 716 through the cannula 710 which extends as a continuation of the first passage portion 730 in the first tubular portion 720.

A first slot 870 (FIG. 16) is formed in the second tubular portion 840 and extends between the inner and outer surfaces of the second tubular portion. The first slot 870 extends in a circumferential direction and along a curvilinear path in the central portion 864 of the second tubular portion 840 toward the end 862 of the second tubular portion. The first slot 870 has a first end 872 located in the central portion 864 of the second tubular portion 840. A second end 874 of the first slot 870 is located adjacent the intersection of the lower edge 846 and the first edge 848 of the arcuate segment 842.

The slot 870 includes a stop portion 876 extending in a distal direction from the second end 874 of the slot. The stop portion 876 extends transverse to the circumferential direction and defines a stop 878. The stop 878 defines a retaining mechanism for resisting movement of the second tubular portion 840 from the expanded condition toward a contracted condition.

A second slot 880 is formed in the second tubular portion 840 and extends between the inner and outer surfaces of the second tubular portion. The second slot 880 extends in a circumferential direction and along a curvilinear path in the central portion 864 of the second tubular portion 840 toward the end 862 of the second tubular portion. The second slot 880 has a first end 882 located in the central portion 864 of the second tubular portion 840. A second end 884 of the second slot 880 is located adjacent the intersection of the lower edge 846 and the second edge 850 of the arcuate segment 842.

The slot 880 includes a stop portion 886 extending in a distal direction from the second end 884. The stop portion 886 extends transverse to the circumferential direction and defines a stop 888. The stop 888 defines the retaining mechanism for resisting movement of the second tubular portion 840 from the expanded condition toward the contracted condition.

The guide member or rivet 791 extends through the first and second slots 870 and 880 in the second tubular portion 840. It is also contemplated that a guide pin or screw could be used instead of the rivet 791. In the tubular configuration of the second tubular portion 840, the guide member 791 is located in the slots 870 and 880 and is movable along the curvilinear path of the slots.

The rivet 791 extends through the washers 793 and the arcuate slots 870 and 880. One of the washers 793 engages the inner surface 890 of the second tubular portion 840. The other washer 793 engages the outer surface of the second tubular portion 840.

The second tubular portion 840 of the tubular structure is expandable from the contracted condition to the expanded condition. In the contracted condition, the guide member 791 is located in the first ends 872 and 882 of the slots 870 and 880 in the second tubular portion 840. The second passage portion defined by the second tubular portion 840 is cylindrical in shape. The second passage portion has a generally constant diameter which is approximately equal to the diameter of the first tubular portion. Thus, the cross-sectional area of the second passage portion and the second end 862 of the second tubular portion 840 is approximately the same as a cross-sectional area at the first end 860 of the second tubular portion and is approximately the same as a cross-sectional area of the first passage portion 730 in the first tubular portion 720.

In the expanded condition, the guide member 791 is located in the second ends 874 and 884 of the slots 870 and 880. The second tubular portion 840 has a conical configuration. The configuration of the second tubular portion 840 when inside the body of a patient will vary depending on the forces exerted by surrounding tissue. At the second end 862 of the second tubular portion 840, the second passage portion has a diameter which is larger than the diameter of the second passage portion at the first end 860. Thus, in the expanded condition, a cross-sectional area of the second passage portion at the second end 862 of the second tubular portion 840 is greater than the cross-sectional area of the second passage portion at the first end 860 of the second tubular portion.

The guide member 791 may be moved relative to the second tubular portion 840 from the second end portions 874 and 884 of the slots 870 and 880 into the stop portions 876 and 886 of the slots. The stops 878 and 888 engage the guide member 791 to resist movement of the second tubular portion 840 from the expanded condition toward the contracted condition. The guide member 791 is moved into the stop portions 876 and 886 of the slots 870 and 880 by the tether member 798.

According to another aspect of the present invention, the stops 878 and 888 may function as a locking mechanism when guide member 791 is positioned within transversely-oriented stop portions 876 and 886, such that the stops 878 and 888 may engage the guide member 791 and thereby prevent movement of the guide member 791 in a circumferential direction. Consequently, depending upon the width of stop portions 876 and 886, relative movement of the first and second edges 848 and 850 with respect to each other is prevented, thereby maintaining the tubular portion 840 in the predetermined condition, e.g., an expanded or an intermediate condition.

The tether member 798 extends from the guide member 791 along the length of the first and second tubular portions 720 and 840 along the outside of the cannula 710. The tether member 798 may be moved in a distal direction relative to the cannula 710 to move the guide member 791 into the stop portions 876 and 886 of the slots 870 and 880. The tether member 798 may be moved in a proximal direction relative to the cannula 710 to move the guide member 791 out of the stop portions 876 and 886 and into the second ends 874 and 884 to permit contraction of the second tubular portion 840 and removal of the cannula from a body of a patient.

Figure 17:
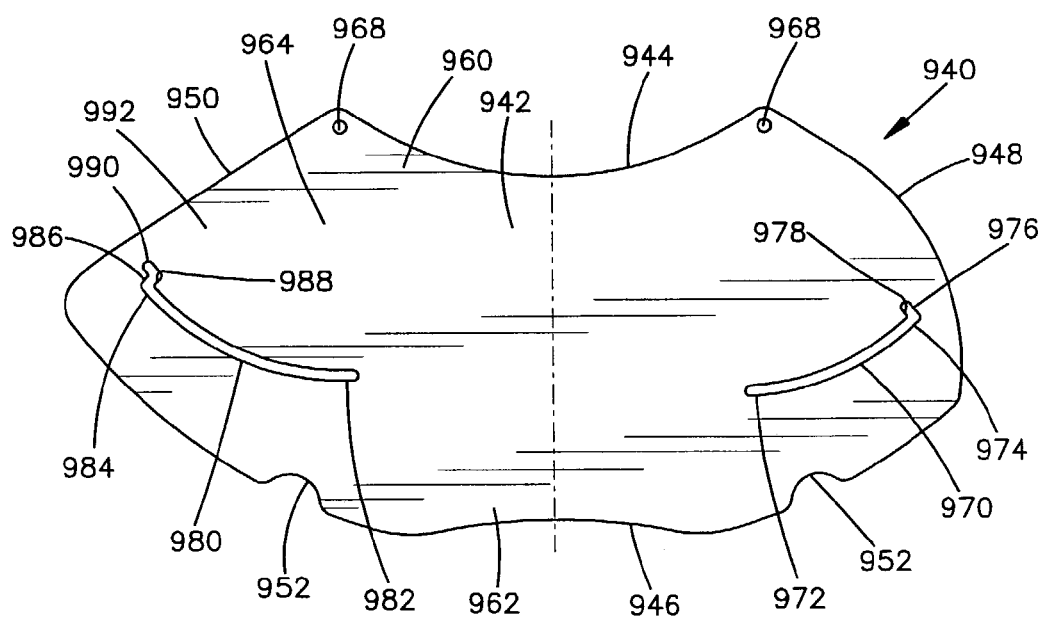
FIG. 17 is a rollout view of another embodiment of an arcuate segment of the cannula of FIG. 14.

Another embodiment of a second tubular portion for use with the first tubular portion 720, illustrated in FIG. 14, is illustrated in FIG. 17. A second tubular portion 940 includes an arcuate segment 942 of sheet stock. The arcuate segment 942 includes upper and lower edges 944 and 946. The arcuate segment 942 also includes first and second edges 948 and 950 extending between the edges 944 and 946. The first and second edges 948 and 950 are rolled in an overlapping manner to form the tubular configuration of the second tubular portion 940. The lower edge 946 includes two semi-circular cut-outs 952 through which a spinal fixation element may pass when the second tubular portion 940 is in an expanded condition.

When the second tubular portion 940 has been rolled into its tubular configuration, the upper and lower edges 944 and 946 define oppositely disposed first and second ends 960 and 962 of the second tubular portion. The first and second ends 960 and 962 are connected by a central portion 964. The first end 960 of the second tubular portion 940 is attached to the distal end 724 of the first tubular portion 720 by a suitable fastener, such as the rivet 766. The rivet 766 extends through two aligned apertures 968 at the first end 960 of the second tubular portion 940. It is also contemplated that a screw could be used instead of the rivet 766.

The second tubular portion 940 includes an inner surface 992 and a parallel outer surface extending between the first and second ends 960 and 962. The inner surface 992 defines a second passage portion of the passage 716 through the cannula 710 which extends as a continuation of the first passage portion 730 in the first tubular portion 720.

A first slot 970 (FIG. 17) is formed in the second tubular portion 940 and extends between the inner and outer surfaces of the second tubular portion. The first slot 970 extends in a circumferential direction and along a curvilinear path in the central portion 964 of the second tubular portion 940 toward the end 962 of the second tubular portion. The first slot 970 has a first end 972 located in the central portion 964 of the second tubular portion 940. A second end 974 of the first slot 970 is located adjacent the intersection of the lower edge 946 and the first edge 948 of the arcuate segment 942.

The slot 970 includes a stop portion 976 extending in a proximal direction from the second end 974 of the slot. The stop portion 976 extends transverse to the circumferential direction and defines a stop 978. The stop 978 defines a retaining mechanism for resisting movement of the second tubular portion 940 from the expanded condition toward a contracted condition.

A second slot 980 is formed in the second tubular portion 940 and extends between the inner and outer surfaces of the second tubular portion. The second slot 980 extends in a circumferential direction and along a curvilinear path in the central portion 964 of the second tubular portion 940 toward the end 962 of the second tubular portion. The second slot 980 has a first end 982 located in the central portion 964 of the second tubular portion 940. A second end 984 of the second slot 980 is located adjacent the intersection of the lower edge 946 and the second edge 950 of the arcuate segment 942.

The slot 980 includes a stop portion 986 extending in a proximal direction from the second end 984. The stop portion 986 extends transverse to the circumferential direction and defines a stop 988. The slot 980 also includes a second portion 990 extending from an end of the stop portion 986 spaced from the second end 984 and transverse to the stop portion. The second portion 990 extends parallel to the circumferential direction. The stop portion 988 and the second portion 990 define a retaining mechanism for resisting movement of the second tubular portion 940 from the expanded condition toward the contracted condition.

The guide member or rivet 791 extends through the first and second slots 970 and 980 in the second tubular portion 940. It is contemplated that a guide pin or screw could be used instead of the rivet 791. In the tubular configuration of the second tubular portion 940, the guide member 791 is located in the slots 970 and 980 and is movable along the curvilinear path of the slots.

The rivet 791 extends through the washers 793 and the arcuate slots 980 and 970. One of the washers 793 engages the inner surface 992 of the second tubular portion. The other washer 793 engages the outer surface of the second tubular portion 940.

The second tubular portion 940 of the tubular structure is expandable from the contracted condition to the expanded condition. In the contracted condition, the guide member 791 is located in the first ends 972 and 982 of the arcuate slots 970 and 980 in the second tubular portion 940. The second passage portion defined by the second tubular portion 940 is cylindrical in shape. The second passage portion has a generally constant diameter which is approximately equal to the diameter of the first tubular portion. Thus, the cross-sectional area of the second passage portion and the second end 962 of the second tubular portion 940 is approximately the same as a cross-sectional area at the first end 960 of the second tubular portion and is approximately the same as a cross-sectional area of the first passage portion 730 in the first tubular portion 720.

In the expanded condition, the guide member 791 is located in the second ends 974 and 984 of the slots 970 and 980. The second tubular portion 940 has a conical configuration. The configuration of the second tubular portion 940 when inside the body of a patient will vary depending on the forces exerted by surrounding tissue. At the second end 962 of the second tubular portion 940, the second passage portion has a diameter which is larger than the diameter of the second passage portion at the first end 960. Thus, in the expanded condition, a cross-sectional area of the second passage portion at the second end 962 of the second tubular portion 940 is greater than the cross-sectional area of the second passage portion at the first end 960 of the second tubular portion.

The guide member 791 may be moved relative to the second tubular portion 940 from the second end portions 974 and 984 of the slots 970 and 980 into the stop portions 976 and 986 of the slots. The stops 978 and 988 engage the guide member 791 to resist movement of the second tubular portion 940 from the expanded condition toward the contracted condition. The guide member 791 may be further moved into the second portion 990 of the slot 980 to further resist movement of the second tubular portion 940 from the expanded condition toward the contracted condition. The guide member 791 is moved into the stop portions 976 and 986 and the second portion 990 of the slot 980 by the tether member 798.

According to another aspect of the present invention, the stops 978, 988 and 990 may function as a locking mechanism when guide member 791 is positioned within transversely-oriented stop portions 976 and 986, e.g., stops 978, 988 and 990 may engage the guide member 791 and thereby prevent movement of the guide member 791 in a circumferential direction. Consequently, depending upon the width of stop portions 976 and 986, relative movement of the first and second edges 948 and 950 with respect to each other is prevented, thereby maintaining the tubular portion 840 in the predetermined condition, e.g., an expanded or an intermediate condition.

The tether member 798 extends from the guide member 791 along the length of the first and second tubular portions 720 and 940 along the outside of the cannula 710. The tether member 798 may be moved in a proximal direction relative to the cannula 710 to move the guide member 791 into the stop portions 976 and 986. The tether member 798 may be moved in a distal direction relative to the cannula 710 to move the guide member 791 out of the stop portions 976 and 986 and into the second ends 974 and 984 to permit contraction of the second tubular portion 940 and removal of the cannula from a body of a patient.

Figure 18:
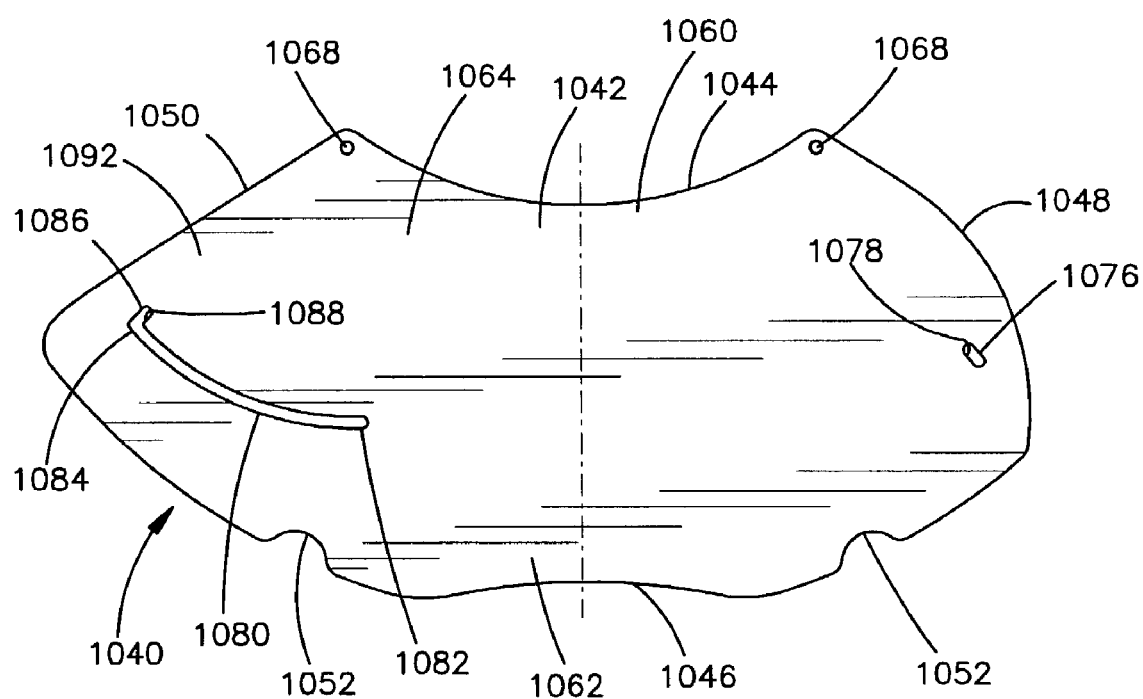
FIG. 18 is a rollout view of another embodiment of an arcuate segment of the cannula of FIG. 14.

Another embodiment of a second tubular portion for use with the first tubular portion 720, illustrated in FIG. 14, is illustrated in FIG. 18. A second tubular portion 1040 is substantially identical to second tubular portion 740, described herein, with the differences noted herein. Second tubular portion 1040 includes an arcuate segment 1042 of sheet stock. The arcuate segment 1042 includes upper and lower edges 1044 and 1046. The arcuate segment 1042 also includes first and second edges 1048 and 1050 extending between the edges 1044 and 1046. The first and second edges 1048 and 1050 are rolled in an overlapping manner to form the tubular configuration of the second tubular portion 1040. The lower edge 1046 includes two semi-circular cut-outs 1052 through which a spinal fixation element may pass when the second tubular portion 1040 is in an expanded condition.

When the second tubular portion 1040 has been rolled into its tubular configuration, the upper and lower edges 1044 and 1046 define oppositely disposed first and second ends 1060 and 1062 of the second tubular portion. The first and second ends 1060 and 1062 are connected by a central portion 1064. The first end 1060 of the second tubular portion 1040 is attached to the distal end 724 of the first tubular portion 720 by a suitable fastener, such as the rivet 766. The rivet 766 extends through two aligned apertures 1068 at the first end 1060 of the second tubular portion 1040. It is also contemplated that a screw could be used instead of the rivet 766.

The second tubular portion 1040 includes an inner surface 1092 and a parallel outer surface extending between the first and second ends 1060 and 1062. The inner surface 1092 defines a second passage portion of the passage 716 through the cannula 710 which extends as a continuation of the first passage portion 730 in the first tubular portion 720.

A first slot 1076 (FIG. 18) is formed in the second tubular portion 1040 and is located adjacent the intersection of the lower edge 1046 and the first edge 1048 of the arcuate segment 1042. The slot 1076 extends transverse to the circumferential direction in a substantially axial direction and defines a stop 1078. The stop 1078 defines a retaining mechanism for resisting movement of the second tubular portion 1040 from the expanded condition toward a contracted condition.

A second slot 1080 is formed in the second tubular portion 1040 and extends between the inner and outer surfaces of the second tubular portion. The second slot 1080 extends in a circumferential direction and along a curvilinear path in the central portion 1064 of the second tubular portion 1040 toward the end 1062 of the second tubular portion. The second slot 1080 has a first end 1082 located in the central portion 1064 of the second tubular portion 1040. A second end 1084 of the second slot 1080 is located adjacent the intersection of the lower edge 1046 and the second edge 1050 of the arcuate segment 1042.

The slot 1080 includes a stop portion 1086 extending in a proximal direction from the second end 1084. The stop portion 1086 extends transverse to the circumferential direction and defines a stop 1088. The stop 1088 defines a retaining mechanism for resisting movement of the second tubular portion 1040 from the expanded condition toward the contracted condition. According to another aspect of the present invention, the stop 1088 may function as a locking mechanism when guide member 791 is positioned within transversely-oriented stop portion 1086, e.g., stop 1088 may engage the guide member 791 and thereby prevent movement of the guide member 791 in a circumferential direction. Depending upon the width of stop portion 1086, relative movement of the first and second edges 1048 and 1050 with respect to each other is prevented, thereby maintaining the tubular portion 1040 in the predetermined condition, e.g., expanded condition or an intermediate condition.

The guide member or rivet 791 extends through the first and second slots 1076 and 1080 in the second tubular portion 1040. It is contemplated that a guide pin or screw could be used instead of the rivet 791. In the tubular configuration of the second tubular portion 1040, the guide member 791 is located in the slots 1076 and 1080 and is movable along the curvilinear path of the slot 1080.

The rivet 791 extends through the washers 793 and the slots 1080 and 1076. One of the washers 793 engages the inner surface 1092 of the second tubular portion. The other washer 793 engages the outer surface of the second tubular portion 1040.

The second tubular portion 1040 of the tubular structure is expandable from the contracted condition to the expanded condition. In the contracted condition, the guide member 791 is located in the first slot 1076 and the first end 1082 of the arcuate slot 1080 in the second tubular portion 1040. The second passage portion defined by the second tubular portion 1040 is cylindrical in shape. The second passage portion has a generally constant diameter which is approximately equal to the diameter of the first tubular portion. Thus, the cross-sectional area of the second passage portion and the second end 1062 of the second tubular portion 1040 is approximately the same as a cross-sectional area at the first end 1060 of the second tubular portion and is approximately the same as a cross-sectional area of the first passage portion 730 in the first tubular portion 720.

In the expanded condition, the guide member 791 remains in slot 1076 and is located in the second end 1084 of the slot 1080. The second tubular portion 1040 has a conical configuration. The configuration of the second tubular portion 1040 when inside the body of a patient will vary depending on the forces exerted by surrounding tissue. At the second end 1062 of the second tubular portion 1040, the second passage portion has a diameter which is larger than the diameter of the second passage portion at the first end 1060.

Thus, in the expanded condition, a cross-sectional area of the second passage portion at the second end 1062 of the second tubular portion 1040 is greater than the cross-sectional area of the second passage portion at the first end 1060 of the second tubular portion.

The guide member 791 may be moved relative to the second tubular portion 1040 from the second end portion 1084 of the slot 1080 into the stop portion 1086 of the second slot 1080 and transversely within the first slot 1076. The stops 1078 and 1088 engage the guide member 791 to resist movement of the second tubular portion 1040 from the expanded condition toward the contracted condition. The guide member 791 is moved into the stop portion 1086 by the tether member 798.

The tether member 798 extends from the guide member 791 along the length of the first and second tubular portions 720 and 1040 along the outside of the cannula 710. The tether member 798 may be moved in a proximal direction relative to the cannula 710 to move the guide member 791 into the stop portions 1076 and 1086. The tether member 798 may be moved in a distal direction relative to the cannula 710 to move the guide member 791 out of the stop portion 1086 and into the second end 1084 to permit contraction of the second tubular portion 1040 and removal of the cannula from a body of a patient.

Figure 19:
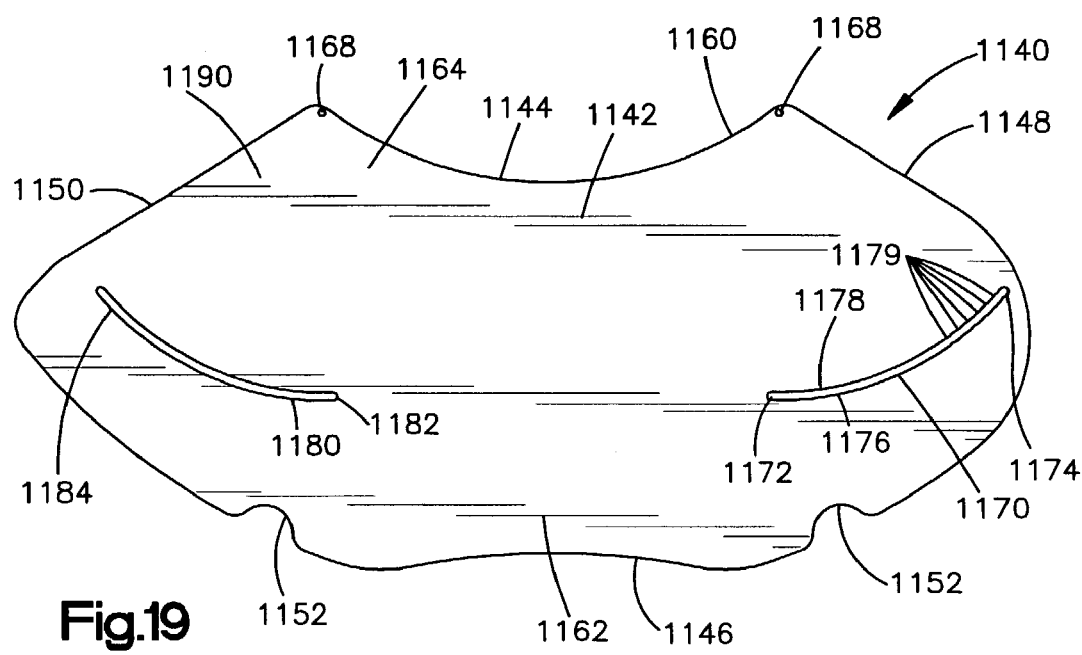
FIG. 19 is a rollout view of another embodiment of an arcuate segment of the cannula of FIG. 14.
Figure 20:
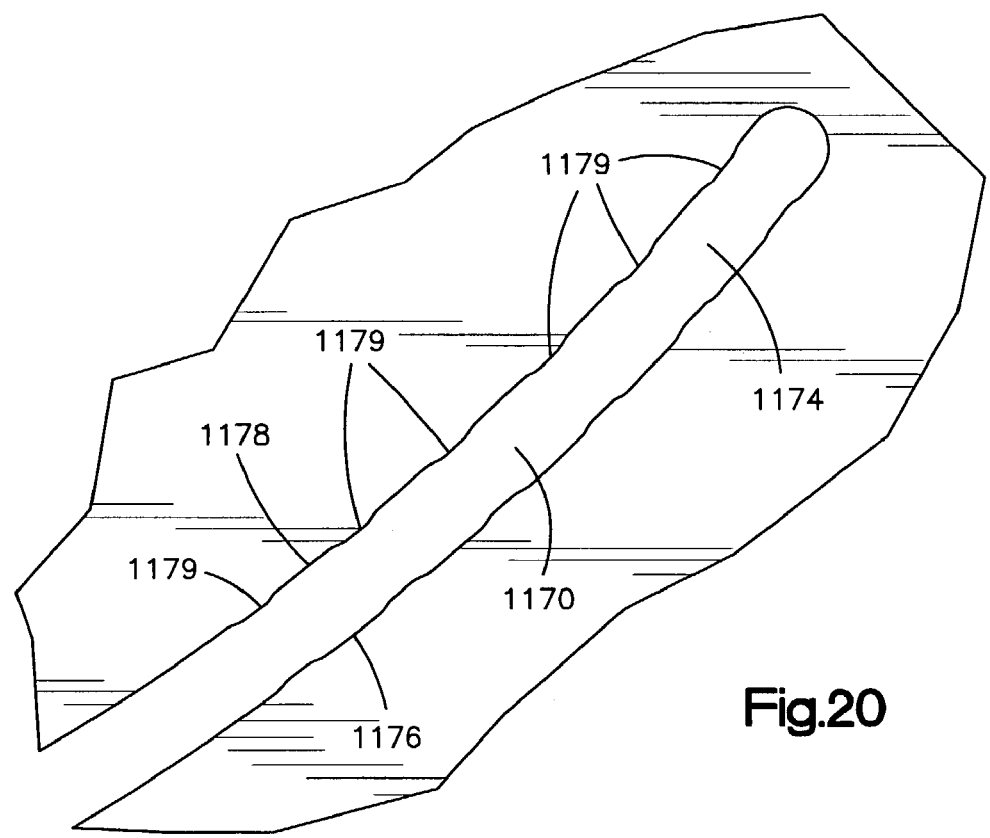
FIG. 20 is an enlarged view of a slot in the arcuate segment of FIG. 19.

Another embodiment of a second tubular portion for use with the first tubular portion 720 of the cannula 710, illustrated in FIG. 14, is illustrated in FIGS. 19 and 20. A second tubular portion 1140 includes an arcuate segment 1142 of sheet stock. The arcuate segment 1142 includes upper and lower edges 1144 and 1146. The arcuate segment 1142 also includes first and second edges 1148 and 1150 extending between the edges 1144 and 1146. The first and second edges 1148 and 1150 are rolled in an overlapping manner to form the tubular configuration of a second tubular portion 1140. The edges 1148 and 1150 are rolled so that the edge 1148 is located on the inside of the second tubular portion 1140 and the edge 1150 is located on the outside of the second tubular portion. The lower edge 1146 includes two semi-circular cutouts 1152 through which a spinal fixation element may pass when the second tubular portion 1140 is in an expanded condition.

When the second tubular portion 1140 has been rolled into its tubular configuration, the upper and lower edges 1144 and 1146 define oppositely disposed first and second ends 1160 and 1162 of the second tubular portion. The first and second ends 1160 and 1162 are connected by a central portion 1164. The first end 1160 of the second tubular portion 1140 is connected to the distal end 724 of the first tubular portion 720 by a suitable fastener, such as the rivet 766. The rivet 766 extends through two aligned apertures 1168 at the first end 1160 of the second tubular portion 1140. It is also contemplated that a screw could be used instead of the rivet 766.

The second tubular portion 1140 includes an inner surface 1190 and a parallel outer surface extending between the first and second ends 1160 and 1162. The inner surface 1190 defines a second passage portion of the passage 716 through the cannula 710 which extends as a continuation of the first passage portion 730 in the first tubular portion 720.

A first slot 1170 (FIG. 19) is formed in the second tubular portion 1140 and extends between the inner and outer surfaces of the second tubular portion. The first slot 1170 extends in a circumferential direction and along a curvilinear path in the central portion 1164 of the second tubular portion 1140 toward the end 1162 of the second tubular portion. The first slot 1170 has a first end 1172 located in the central portion 1164 of the second tubular portion 1164 of the second tubular portion 1140. A second end 1174 of the first slot 1170 is located adjacent the intersection of the lower edge 1146 and the first edge 1148 of the arcuate segment 1142.

The first slot 1170 is defined by opposite edges 1176 and 1178. The edges 1176 and 1178 are spaced apart a first distance adjacent the first end 1172 of the slot 1170. The opposite edges 1176 and 1178 (FIG. 20) are spaced apart a second distance, which is less than the first distance, at six locations along the slot 1170 to define six stops 1179 between the ends 1172 and 1174. The stops 1179 define six expanded conditions of the second tubular portion 1140. The stops 1179 at least partially define a retaining mechanism for resisting movement of the second tubular portion 1140 from the expanded conditions toward a contracted condition and/or another expanded condition. The stops 1179 extend in directions transverse to the circumferential direction in which the slot 1170 extends. Although the present invention shows six stops 1179, it is contemplated that the slot 1170 could have any number of stops.

A second slot 1180 (FIG. 19) is formed in the second tubular portion 1140 and extends between the inner and outer surfaces of the second tubular portion. The second slot 1180 extends in a circumferential direction and along a curvilinear path in the central portion 1164 of the second tubular portion 1140 toward the end 1162 of the second tubular portion. The second slot 1180 has a first end 1182 located in the central portion 1164 of the second tubular portion 1140. A second end 1184 of the second slot 1180 is located adjacent the intersection of the lower edge 1146 and the second edge 1150 of the arcuate segment 1142. Although the edges of the second slot 1180 do not define stops, it is contemplated that opposite edges of the slot 1180 may define stops similar to stops 1179.

The guide member or rivet 791 extends through the first and second slots 1170 and 1180 in the second tubular portion 1140. It is also contemplated that a guide pin or screw could be used instead of the rivet 791. In the tubular configuration of the second tubular portion 1140, the guide member 791 is located in the slots 1170 and 1180 and is moveable along the curvilinear path of the slots.

The rivet 791 extends through the washers 793 and the arcuate slots 1170 and 1180. One of the washers 793 engages the inner surface 1190 of the second tubular portion 1140. The other washer 793 engages the outer surface of the second tubular portion 1140.

The second tubular portion 1140 of the tubular structure is expandable from the contracted condition to any one of six expanded conditions. In the contracted condition, the guide member 791 is located in the first ends 1172 and 1182 of the slots 1170 and 1180 in the second tubular portion 1140. The second passage portion defined by the second tubular portion 1140 is cylindrical in shape. The second passage portion has a generally constant diameter which is approximately equal to the diameter of the first tubular portion. Thus, the cross-sectional area of the second passage portion and the second end 1162 of the second tubular portion 1140 is approximately the same as a cross-sectional area at the first end 1160 of the second tubular portion and is approximately the same as a cross-sectional area of the first passage portion 730 in the first tubular portion 720.

In the expanded conditions, the guide member 791 engages one of the stops 1179 in the first slot 1170. The stops 1179 retain the guide member 791 in one of a plurality of positions relative to the slots 1170 and 1180 and resist movement of the guide member from one of the plurality of positions relative to the slots. Accordingly, the stops 1179 resist contraction and/or expansion of the second tubular portion 1140. A tether member is not needed to move the guide member 791 into the stops 1179.

The second tubular portion 1140 has a conical configuration when in the expanded conditions. The configuration of the second tubular portion 1140 when inside the body of a patient will vary depending on the forces exerted by surrounding tissue. At the second end 1162 of the second tubular portion 1140, the second passage portion has a diameter which is larger than the diameter of the second passage portion at the first end 1160. Thus, in the expanded conditions, a cross-sectional area of the second passage portion at the second end 1062 of the second tubular portion 1140 is greater than the cross-sectional area of the second passage portion at the first end 1160 of the second tubular portion.

During a surgical procedure, the cannula 710 is inserted over a dilator and through an incision into the body of a patient in the contracted condition. The second tubular portion 1140 is inserted inside the body. The first tubular portion 720 is inserted into the incision so that the first tubular portion extends from an exterior of the body to inside the body. A member, such as heat shrunk tubing, for maintaining the second tubular portion 1140 in the contracted condition is torn after insertion of the cannula.

An expansion tool (not shown) is inserted into the passage 716 in the cannula 710. The expansion tool is manually operated, causing a radially outwardly directed force to be exerted on the inner surface 1190 of the second tubular portion 1140 by the tool. The second tubular portion 1140 expands toward one of the expanded conditions. Under the force of the expansion tool, the guide member 791 slides from the first ends 1172 and 1182 of the slots 1170 and 1180 toward the second ends 1174 and 1184 of the slots to permit the expansion of the second tubular portion 1140. The guide member 791 engages a first stop 1179 to position the guide member relative to the slots 1170 and 1180. If the second tubular portion 1140 needs to be expanded further, additional force is applied to the second tubular portion to move the guide member 791. Expansion of the second tubular portion 1140 can be stopped when the guide member 791 engages any of the stops 1179. The guide member 791 engages the stops 1179 to position the guide member in any one of the plurality of positions relative to the slots 1170 and 1180. The stops 1179 resist movement of the guide member 791 relative to the slots 1170 and 1180. Accordingly, the second tubular portion 1140 has a plurality of expanded conditions. The expansion tool is then removed so that one or more surgical instruments can be received through the cannula 710 and inserted into a patient's body.

Upon conclusion of the surgical procedure, the cannula 710 is removed from the incision. The cannula 710 is moved in a proximal direction relative to the body of the patient. The surrounding tissue of the body exerts forces on the second tubular portion 1140 that are large enough to contract the second tubular portion while the cannula is moving in the proximal direction. Accordingly, the guide member 791 moves toward the first ends 1172 and 1182 of the slots 1170 and 1180 as the cannula 710 is moved in the proximal direction.

It is contemplated that the second tubular portions disclosed in FIGS. 1–6 and 14–20 may have one or two slots that define stops. If the second tubular portion has two slots, it is contemplated that either one or both slots could define stops. Furthermore, it is contemplated that the slots could have stop portions as disclosed in FIGS. 14–17 and define stops as disclosed in FIGS. 1–6 or FIGS. 19–20.

From the above description of the invention, those skilled in the art will perceive improvements, changes and modifications. Such improvements, changes and modifications within the skill of the art are intended to be covered by the appended claims.

Having described the invention, the following is claimed:

1. A structure for receiving surgical instruments for performing a surgical procedure on a body, said structure comprising:
   a portion defining a passage through which the surgical instruments are inserted into the body, said passage having a proximal end and a distal end;
   an expandable portion for enabling an increase in a cross-sectional area of said distal end of said passage;
   said expandable portion having a contracted condition in which the cross-sectional area of said distal end of said passage has a first cross-sectional area, said expandable portion having an expanded condition in which said distal end of said passage has a second cross-sectional area greater than said first cross-sectional area, and said second cross-sectional area being greater than a cross-sectional area of said proximal end of said passage when said expandable portion is in said expanded condition; and
   a retaining mechanism for resisting movement of said expandable portion from said expanded condition toward said contracted condition, said retaining mechanism comprising an edge extending at least partially between an outer surface and an inner surface of the expandable portion, said edge of said retaining mechanism being generally transverse to said outer and inner surfaces of the expandable portion, said edge of said retaining mechanism increasing resistance to movement of the expandable portion from said expanded condition toward said contracted condition, when the expandable portion is in said expanded condition, by interlocking with an edge of the expandable portion.

2. A structure as defined in claim 1 wherein said proximal end of said passage has a cross-sectional area that remains substantially constant.

3. A structure as defined in claim 1 wherein said structure has a first portion and a second portion connected to a distal end of said first portion, said second portion including said expandable portion.

4. A structure as defined in claim 3 wherein said second portion is pivotable relative to said first portion.

5. A structure as defined in claim 1 wherein said expandable portion has a slot and a guide member disposed in said slot, said guide member being movable from a first end of said slot toward a second end of said slot to enable the cross-sectional area of said distal end of said passage to increase, said expandable portion having a stop engageable with said guide member to define said retaining mechanism and resist movement of said guide member from said second end of said slot toward said first end of said slot.

6. A structure as defined in claim 5 wherein said expandable portion has a plurality of stops engageable with said guide member.

7. A structure as defined in claim 5 wherein said slot is defined by opposite edges, said opposite edges being spaced apart a first distance at a first portion of said slot, and said opposite edges being spaced apart a second distance less than the first distance at a second portion of said slot to define said stop.

8. A structure as defined in claim 5 wherein said slot extends in a circumferential direction from said first end to said second end, said slot including a stop portion extending transverse to said circumferential direction, said stop portion of said slot defining said stop.

9. A structure as defined in claim 8 further including a member connected with one of said guide member and said expandable portion for moving said guide member relative to said expandable portion and into said stop portion of said slot.

10. A structure as defined in claim 9 wherein said member extends along said structure outside said passage.

11. A structure as defined in claim 9 wherein said member is connected with said guide member.

12. A structure as defined in claim 8 wherein said stop portion of said slot extends in a proximal direction from said second end of said slot.

13. A structure as defined in claim 8 wherein said stop portion of said slot extends in a distal direction from said second end of said slot.

14. A structure as defined in claim 8 wherein said slot includes a second portion extending from an end of said stop portion spaced from said second end of said slot and transverse to said stop portion, said second portion further defining said retaining mechanism.

15. A structure as defined in claim 14 wherein said second portion extending from said end of said stop portion extends parallel to the circumferential direction in which said slot extends.

16. A structure as defined in claim 1 wherein said expandable portion includes first and second overlapping portions, said first portion moving relative to said second portion as said expandable portion moves from said contracted condition to said expanded condition.

17. A structure as defined in claim 16 further including a guide member disposed in a first slot in said first portion and disposed in a second slot in said second portion, said guide member being movable from first ends of said first and second slots toward second ends of said first and second slots to enable the cross-sectional area of said distal end of said passage to increase.

18. A structure as defined in claim 17 wherein said expandable portion has a stop engageable with said guide member to define said retaining mechanism and resist movement of said guide member from said second ends toward said first ends, one of said first and second slots having a stop portion extending from said second end of said one of said first and second slots and transverse to said circumferential direction, said stop portion defining said stop.

19. A structure as defined in claim 18 further including a member connected to one of said guide member and said expandable portion for moving said guide member relative to said expandable portion and into said stop portion of said one of said first and second slots.

20. A structure as defined in claim 19 wherein said member extends along said structure outside said passage.

21. A structure as defined in claim 19 wherein said member is connected with said guide member.

22. A structure as defined in claim 18 wherein each of said first and second slots has a stop portion extending from said second end transverse to said circumferential direction.

23. A structure as defined in claim 22 wherein said stop portions extend in proximal directions from said second ends of said first and second slots.

24. A structure as defined in claim 22 wherein said stop portions extend in distal directions from said second ends of said first and second slots.

25. A structure as defined in claim 22 wherein one of said first and second slots includes a second portion extending from an end of said stop portion spaced from said second end and transverse to said stop portion.

26. A structure as defined in claim 25 wherein said second portion extending from said end of said stop portion extends parallel to said circumferential direction.

27. A structure as defined in claim 1 wherein said structure is tubular.

28. A structure as defined in claim 1 wherein said expandable portion includes a plurality of expanded conditions, said retaining mechanism resisting movement of said expandable portion from each of said plurality of expanded conditions toward said contracted condition.

29. A structure as defined in claim 1 further including a member for releasing said retaining mechanism to permit movement of said expandable portion from said expanded condition toward said contracted condition.

30. A structure as defined in claim 1 wherein said edge or surface of the expandable portion is provided on a pin.

31. A structure as defined in claim 1, further comprising a pin that interlocks with the edge of said retaining mechanism.

32. A structure for receiving surgical instruments for performing a surgical procedure on a body, said structure comprising:
a passage through which the surgical instruments are inserted into the body, said passage having a proximal end and a distal end;
an expandable portion for enabling an increase in a cross-sectional area of said distal end of said passage;
said expandable portion having a contracted condition in which the cross-sectional area of said distal end of said passage has a first cross-sectional area, said expandable portion having an expanded condition in which said distal end of said passage has a second cross-sectional area greater than said first cross-sectional area, and said second cross-sectional area being greater than a cross-sectional area of said proximal end of said passage when said expandable portion is in said expanded condition, said expandable portion having a slot and a guide member disposed in said slot, said guide member being movable from a first end of said slot toward a second end of said slot to enable the cross-sectional area of said distal end of said passage to increase, said slot extending in an arcuate direction from said first end to said second end, said slot including a stop portion extending in a direction generally transverse to a length of the slot, and said stop portion being located between the first end and the second end of said slot, said stop portion of said slot configured to interlock with said guide member to define a retaining mechanism for resisting movement of said guide member toward said first end of said slot and movement of said expandable portion from said expanded condition toward said contracted condition.

33. A structure as defined in claim 32 wherein said proximal end of said passage has a cross-sectional area that remains substantially constant.

34. A structure as defined in claim 32 further including a member connected with one of said guide member and said expandable portion for moving said guide member relative to said expandable portion and into said stop portion of said slot.

35. A structure as defined in claim 34 wherein said member extends along said structure outside said passage.

36. A structure as defined in claim 34 wherein said member is connected with said guide member.

37. A structure as defined in claim 32 wherein said stop portion of said slot extends in a proximal direction from said slot.

38. A structure as defined in claim 32 wherein said stop portion of said slot extends in a distal direction from said slot.

39. A structure as defined in claim 32 wherein said slot includes a second portion extending from an end of said stop portion transverse to said stop portion, said second portion further defining said retaining mechanism.

40. A structure as defined in claim 39 wherein said second portion extending from said end of said stop portion extends parallel to the circumferential direction in which said slot extends.

41. A structure as defined in claim 32 wherein said expandable portion includes first and second overlapping portions, said first portion moving relative to said second portion as said expandable portion moves from said contracted condition to said expanded condition.

42. A structure as defined in claim 41 wherein said guide member is disposed in a first slot in said first portion and disposed in a second slot in said second portion, said guide member being pivotable from first ends of said first and second slots toward second ends of said first and second slots to enable the cross-sectional area of said distal end of said passage to increase, one of said first and second slots having said stop portion extending transverse to said circumferential direction.

43. A structure as defined in claim 42 further including a member connected to one of said guide member and said expandable portion for moving said guide member relative to said expandable portion and into said stop portion of said one of said first and second slots.

44. A structure as defined in claim 42 wherein said member is connected with said guide member.

45. A structure as defined in claim 42 wherein each of said first and second slots has a stop portion extending transverse to said circumferential direction.

46. A structure as defined in claim 45 wherein said stop portions extend in proximal directions from said first and second slots.

47. A structure as defined in claim 45 wherein said stop portions extend in distal directions from said first and second slots.

48. A structure as defined in claim 45 wherein one of said first and second slots includes a second portion extending from an end of said stop portion and transverse to said stop portion.

49. A structure as defined in claim 48 wherein said second portion extending from said end of said stop portion extends parallel to said circumferential direction.

50. A structure as defined in claim 32 further including a member for moving said guide member out of engagement with said stop to permit movement of said expandable portion from said expanded condition toward said contracted condition.

51. A structure for receiving surgical instruments for performing a surgical procedure on a body, said structure comprising:
 a portion defining a passage through which the surgical instruments are inserted into the body, said passage having a proximal end and a distal end;
 an expandable portion for enabling an increase in a cross-sectional area of said distal end of said passage; said expandable portion having a contracted condition in which the cross-sectional area of said distal end of said passage has a first cross-sectional area, said expandable portion having an expanded condition in which said distal end of said passage has a second cross-sectional area greater than said first cross-sectional area; and
 a notch configured to prevent movement of said expandable portion from a contracted condition to an expanded condition or from an expanded condition to a contracted condition, said notch being configured to lockingly engage with an edge of a transverse member to increase resistance to movement of the expandable portion from either the expanded or contracted condition toward one of said contracted condition and said expanded condition.

52. A structure as defined in claim 51 wherein said notch is located adjacent said expandable portion.

53. A structure as defined in claim 52 further comprising a guide member engageable with a stop formed by said notch defining a stop portion of a slot in said expandable portion.

54. A structure as defined in claim 53 wherein said expandable portion has a circumferential portion of said slot in communication with said stop portion of said slot and said guide member is movable within said circumferential portion and said stop portion, said guide member being movable within said circumferential portion to enable the cross-sectional area of said distal end of said passage to change.

55. A structure as defined in claim 54 further including a member connected with one of said guide member and said expandable portion for moving said guide member relative to said expandable portion and into said stop portion of said slot.

56. A structure as defined in claim 55 wherein said member extends along said structure outside said portion defining the passage.

57. A structure as defined in claim 55 wherein said member is connected with said guide member.

58. A structure as defined in claim 54 wherein said stop portion extends in a proximal direction from said circumferential portion of said slot.

59. A structure as defined in claim 54 wherein said stop portion extends in a distal direction from said circumferential portion of said slot.

60. A structure as defined in claim 54 wherein said slot includes a second portion extending from an end of said stop portion spaced from said circumferential portion and transverse to said stop portion.

61. A structure as defined in claim 60 wherein said second portion extending from said end of said stop portion extends substantially parallel to the circumferential direction in which said circumferential portion of said slot extends.

62. A structure as defined in claim 51 wherein said expandable portion comprises first and second overlapping portions, said first overlapping portion moving relative to said second overlapping portion as said expandable portion moves between said contracted condition and said expanded condition.

63. A structure as defined in claim 62 further comprising a guide member engageable with a slop formed by said notch defining a stop portion of a first slot in one of said first and second overlapping portions to prevent relative movement of said first overlapping portion with respect to said second overlapping portion.

64. A structure as defined in claim 62 further comprising a guide member engageable with a stop formed by said notch defining a stop portion of a first slot in one of said first and second overlapping portions to prevent relative movement of said first overlapping portion with respect to said second overlapping portion beyond a predetermined range of movement.

65. A structure as defined in claim 62 wherein said guide member is further disposed in a second slot in said second overlapping portion, said guide member being movable within one of the first and second slots to enable the cross-sectional area of said distal end of said passage to change.

66. A structure as defined in claim 51, further comprising an inflection point located between the arcuate portion and the notch.

67. A structure as defined in claim 51 wherein said transverse member comprises at least a portion of the expandable portion.

68. A structure as defined in claim 51 wherein said transverse member comprises a pin.

69. A device for providing access to a spinal location within a patient, said device comprising:
an elongate body having a proximal end and a distal end and defining a length between the proximal and distal ends such that the proximal end can be positioned outside the patient and the distal end can be positioned inside the patient adjacent the spinal location, said elongate body having a contracted configuration and an expanded configuration, wherein the cross-sectional area of said body at a first location of the expanded configuration is greater than the cross-sectional area of said body at a second location of the expanded configuration, wherein the first location is distal to the second location;
said elongate body comprising a first member and a second member movable relative to said first member, said first member comprising a notch to retain said second member in a position relative to said first member when said elongate body is in the expanded configuration, said notch having a transverse component relative to a direction of movement of the second member that is configured to interlock with said second member to thereby increase resistance to movement of the second member adjacent the notch as the elongate body moves from the expanded configuration to the contracted configuration.

70. The device of claim 69, wherein said notch retains said elongate body in its expanded configuration.

71. The device of claim 69, wherein said elongate body is metal.

72. The device of claim 69, wherein said first member comprises a plurality of notches.

73. The device of claim 69, wherein said first member and said second member overlap at least at the distal end of the elongate body.

74. The device of claim 69, wherein said second member comprises a guide member engageable with said notch.

75. The device of claim 69, wherein the configuration of the elongate body between the first location and the second location is conical when the elongate body is inserted within the patient.

76. The device of claim 69, wherein the first location is at a distal end of the elongate body, and the second location is at a proximal end of the elongate body.

77. The device of claim 69, wherein the elongate body is configured to be inserted through the skin of the patient and is sized to provide access to a spinal location.

78. The device of claim 69, wherein the elongate body comprises rigid material extending around substantially the entire perimeter of the cross-sectional area between the proximal and distal ends.

79. The device of claim 69, wherein the body is sized such that more than one surgical instrument can be positioned simultaneously through the body.

80. The device of claim 69, wherein the body is defined by a smooth metal inner surface extending at least partially around a passage between the proximal and distal ends.

81. The device of claim 69, wherein an outer surface of the elongate body at least partially overlaps the inner surface of the elongate body in the contracted configuration, and the elongate body is actuatable to the expanded configuration by reducing the overlap between the inner and outer surfaces along a pivot joint between adjacent portions of the elongate body, and wherein the notch maintains the elongate body in the expanded configuration after actuation to the expanded configuration.

82. The device of claim 69, wherein the elongate body is configured to be manually expanded.

83. The device of claim 82, wherein the body is sized to receive an expander tool adapted to manually expand said elongate body.

84. The device of claim 69, wherein the elongate body defines a length between the proximal and distal ends such that the proximal end can be positioned outside the patient.

85. A device for providing access to a spinal location within a patient, said device comprising:
an elongate body for providing access to a spinal location having a proximal end and a distal end and defining a length between the proximal and distal ends such that the proximal end can be positioned outside the patient and the distal end can be positioned inside the patient adjacent the spinal location, said elongate body having an outer surface and an inner surface, said elongate body being expandable from a contracted configuration to an expanded configuration, wherein the cross-sectional area of said body at a first location is greater than the cross-sectional area of said body at a second location in the expanded configuration, wherein the first location is distal to the second location; and
a guiding mechanism comprising at least three notches along a length of the guiding mechanism, the notches located between, and spaced from, a first end of the guiding mechanism and a second end of the guiding mechanism, whereby the elongate body moves from its contracted condition to its expanded condition by being guided incrementally along successive notches.

86. The device of claim 85, wherein the elongate body is capable of having a plurality of incrementally larger expanded configurations when inserted within the patient, each of said configurations being defined by expansion of said elongate body to one of said notches.

87. The device of claim 85, wherein the elongate body comprises a first member and a second member moveable relative to each other.

88. The device of claim 85, wherein the guiding mechanism comprises a slot and a member moveable within said slot.

89. The device of claim 88, wherein the notches are provided along said slot.

90. The device of claim 85, wherein the guiding mechanism is provided in the surfaces of the elongate body.

91. The device of claim 85, wherein the elongate body in the contracted configuration farms a tube having a circular cross-section.

* * * * *

UNITED STATES PATENT AND TRADEMARK OFFICE
CERTIFICATE OF CORRECTION

PATENT NO. : 7,144,393 B2 Page 1 of 1
APPLICATION NO. : 10/361887
DATED : December 5, 2006
INVENTOR(S) : Gene P. DiPoto It is certified that error appears in the above-identified patent and that said Letters Patent is hereby corrected as shown below:

Column 30, line 59, before "formed" delete "slop" and insert --stop--.

Signed and Sealed this

Twenty-seventh Day of March, 2007

JON W. DUDAS
*Director of the United States Patent and Trademark Office*